US006121005A

United States Patent [19]
Fournier et al.

[11] Patent Number: 6,121,005
[45] Date of Patent: Sep. 19, 2000

[54] POLYPEPTIDES COMPRISING DOMAINS OF THE GAX PROTEIN IMPLICATED IN THE REPRESSION OF TRANSCRIPTION AND/OR INTERACTION WITH OTHER PROTEINS, CORRESPONDING NUCLEIC ACIDS, AND THEIR USE

[75] Inventors: Alain Fournier, Chatenay Malabry; Abderrahim Mahfoudi, Marolles en Brie; Christophe Marcireau, Paris; Didier Branellec, La Varenne Saint-Hilaire, all of France

[73] Assignee: Aventis Pharma S.A., Antony Cedex, France

[21] Appl. No.: 08/950,860

[22] Filed: Oct. 15, 1997

[30] Foreign Application Priority Data

Oct. 18, 1996 [FR] France .................................. 96 12730

[51] Int. Cl.$^7$ ........................... C07K 14/47; G01N 33/53
[52] U.S. Cl. ............................. 435/7.1; 530/324; 530/350
[58] Field of Search ................................. 435/7.1; 514/2; 530/300, 324, 350

[56] References Cited

FOREIGN PATENT DOCUMENTS

WO 95/23161  8/1995  WIPO.
WO 95/30385  10/1996  WIPO.
WO 97/16459  5/1997  WIPO.

OTHER PUBLICATIONS

LePage et al., Molecular Cloning and Localization of the Human GAX Gene to 7p21, Genomics 24, 535–540 (1994).
Gorski et al., Molecular Cloning of a Diverged Homebox Gene That Is Rapidly Down–Regulated during the G0/G1 Transition in Vascular Smooth Muscle Cells, Molecular & Cellular Biology, 13(6), 3722–3733 (1993).
Gehring et al., Homedomain–DNA Recognition, Cell 78, 211–223 (1994).
Weir et al., GAX is Rapidly Downregulated in Rat Carotid Arteries Following Balloon Injury: In Vivo Demonstration of a Growth–Arrest Transcription Factor, Abstracts From the 67th Scientific Sessions, Circ. 90 (4 Part 2) (1994).
Walsh et al., Cell Cycle Control by the GAX Homebox Protein in Vascular Smooth Muscle Cells, Abstracts From the 67th Scientific Sessions, Circ. 90 (4 Part 2) (1994).
Branellec et al.. A Recombinant Adenovirus Encoding GAX Efficiently Block Vascular Smooth Muscle Cell Proliferation, Supplement I, Circ. 92(8), (1995).
Gorski et al., Mitogen–responsive nuclear factors that mediate growth control signals in vascular myocytes, Cardiovascular Research 30, 585–592 (1995).
Lawrence et al., Homeobox Genes: Their Function in Drosophila Segmentation and Pattern Formation, Cell 78, 181–189 (1994).
Krumlauf, Hox Genes in Vertebrate Development, Cell 78, 191–201 (1994).
Fukuda et al., Structure–Function Relationship of the Eukaryotic DNA Replication Factor, Proliferating Cell Nuclear Antigen, The Journal of Biological Chemistry, 270(38), 22527–22534 (1995).
Nikaido et al., Loss in Transformed Cells of Cell Regulation of Expression of a Nuclear Protein Recoginzed by SLE Patient Antisera, Experimental Cell Research 182, 284–289 (1989).
Nikaido et al., Cloning and nucleotide sequence of cDNA for Ki antigen, a highly conserved nuclear protein detected with sera from patients with systemic erythermatosus, Clin. Exp. Immunol. 79,209–214 (1990).
Almendral et al., Cloning and sequence of the human nuclear protein cyclin: Homology with DNA–binding proteins, Proc. Natl. Acad. Sci., 84 1575–1579 (1987).
Takeuchi et al.. Molecular Interaction Between Proliferating Cell Nuclea Antigen and Ki Autoantigen Recognized By Sera From Patients With Systemic Lupus Erythematosus, Abstract Juntendo Universssity, Tokyo, Japan 1995).

*Primary Examiner*—Robert A. Schwartzman
*Attorney, Agent, or Firm*—Finnegan, Henderson, Farabow, Garrett & Dunner, L.L.P.

[57] ABSTRACT

This invention pertains to polynucleotides comprising GAX domains involved in GAX biological activity. It may pertain, notably, to domains involved in the interaction of GAX with other molecules or domains that are responsible for biological activity. The invention also pertains to chimeric molecules comprising a GAX functional domain. It also pertains to the use of GAX to repress gene expression, as well as the use of compounds that inhibit GAX interaction with certain cellular partners to modulate GAX activity. It also pertains to a method for screening and/or identifying GAX cellular partners.

11 Claims, 7 Drawing Sheets

A

B

SEQUENCE LISTING

<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:  Sequencing
      Oligonucleotide Complementary to GAL4TA

<400> SEQUENCE: 1
ctattcgatg atgaagatac ccc                                                 23

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:  Synthetic
      Oligonucleotide Encoding a myc tag Sequence

```
<400> SEQUENCE: 2
catcaagctt atggagcaga agctgatctc cgaggaggac ctgcagcttc        50

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence:  Synthetic
      Oligonucleotide Encoding a myc tag Sequence

<400> SEQUENCE: 3 atggatcca cgtgcaggtc ctcctcggag atcagcttct gctccataag ctt    53

<210> SEQ ID NO 4
<211> LENGTH: 25
<212> TYPE: DNA
<213> ORGANISM: Homo sapiens

<400> SEQUENCE: 4
cgcggatccc atggcctcgt tgctg                                   25

<210> SEQ ID NO 5
<211> LENGTH: 30
<212> TYPE: DNA
<213> ORGANISM: Homo sapiens

<400> SEQUENCE: 5
gtagagctcg agtcagtaca gagtctctgc                              30

<210> SEQ ID NO 6
<211> LENGTH: 30
<212> TYPE: DNA
<213> ORGANISM: Mus musculus

<400> SEQUENCE: 6
gagcgaattc atgaccatga cccttcacac                              30

<210> SEQ ID NO 7
<211> LENGTH: 30
<212> TYPE: DNA
<213> ORGANISM: Mus musculus

<400> SEQUENCE: 7
gagcgaattc actgatcgtg ttggggaagc                              30

<210> SEQ ID NO 8
<211> LENGTH: 60
<212> TYPE: DNA
<213> ORGANISM: Mus musculus

<400> SEQUENCE: 8
tcgagaggtc atattgacct aagcttcggg tcggagtact gtcctccgac tgccatatgt    60

<210> SEQ ID NO 9
<211> LENGTH: 60
<212> TYPE: DNA
<213> ORGANISM: Mus musculus

<400> SEQUENCE: 9
ctagacatat ggcagtcgga ggacagtact ccgacccgaa gcttaggtca atatgacctc    60

<210> SEQ ID NO 10
```

-continued

```
<211> LENGTH: 34
<212> TYPE: DNA
<213> ORGANISM: Homo sapiens

<400> SEQUENCE: 10
cgcggaattc tgttcgaggc gcgcctggtc cagg                                34

<210> SEQ ID NO 11
<211> LENGTH: 8
<212> TYPE: PRT
<213> ORGANISM: Homo sapiens

<400> SEQUENCE: 11

Phe Glu Ala Arg Leu Val Gln Gly
  1               5

<210> SEQ ID NO 12
<211> LENGTH: 34
<212> TYPE: DNA
<213> ORGANISM: Homo sapiens

<400> SEQUENCE: 12
ggtcgaattc taagatcctt cttcatcctc gatc                                34

<210> SEQ ID NO 13
<211> LENGTH: 8
<212> TYPE: PRT
<213> ORGANISM: Homo sapiens

<400> SEQUENCE: 13

Ser Gly Glu Glu Asp Glu Ile Lys
  1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:  Synthetic
      Cationic Polymer

<400> SEQUENCE: 14

Leu Lys Leu Lys
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:  Synthetic
      Cationic Polymer

<400> SEQUENCE: 15

Leu Lys Lys Leu
  1

<210> SEQ ID NO 16
<211> LENGTH: 302
<212> TYPE: PRT
<213> ORGANISM: Homo sapiens

<400> SEQUENCE: 16

Met Glu His Pro Leu Phe Gly Cys Leu Arg Ser Pro His Ala Thr Ala
  1               5                  10                  15
```

-continued

```
Gln Gly Leu His Pro Phe Ser Gln Ser Ser Leu Ala Leu His Gly Arg
            20                  25                  30

Ser Asp His Met Ser Tyr Pro Glu Leu Ser Thr Ser Ser Ser Ser Cys
            35                  40                  45

Ile Ile Ala Gly Tyr Pro Asn Glu Glu Asp Met Phe Ala Ser Gln His
        50                  55                  60

His Arg Gly His His His His His His His His His His Gln Gln
 65              70                  75                  80

Gln Gln His Gln Ala Leu Gln Thr Asn Trp His Leu Pro Gln Met Ser
            85                  90                  95

Ser Pro Pro Ser Ala Ala Arg His Ser Leu Cys Leu Gln Pro Asp Ser
            100                 105                 110

Gly Gly Pro Pro Glu Leu Gly Ser Ser Pro Pro Val Leu Cys Ser Asn
            115                 120                 125

Ser Ser Ser Leu Gly Ser Ser Thr Pro Thr Gly Ala Ala Cys Ala Pro
    130                 135                 140

Gly Asp Tyr Gly Arg Gln Ala Leu Ser Pro Ala Glu Ala Glu Lys Arg
145                 150                 155                 160

Ser Gly Gly Lys Arg Lys Ser Asp Ser Ser Asp Ser Gln Glu Gly Asn
                165                 170                 175

Tyr Lys Ser Glu Val Asn Ser Lys Pro Arg Lys Glu Arg Thr Ala Phe
            180                 185                 190

Thr Lys Glu Gln Ile Arg Glu Leu Glu Ala Glu Phe Ala His His Asn
            195                 200                 205

Tyr Leu Thr Arg Leu Arg Arg Tyr Glu Ile Ala Val Asn Leu Asp Leu
    210                 215                 220

Thr Glu Arg Gln Val Lys Val Trp Phe Gln Asn Arg Arg Met Lys Trp
225                 230                 235                 240

Lys Arg Val Lys Gly Gly Gln Gln Gly Ala Ala Ala Arg Glu Lys Glu
                245                 250                 255

Leu Val Asn Val Lys Lys Gly Thr Leu Leu Pro Ser Glu Leu Ser Gly
            260                 265                 270

Ile Gly Ala Ala Thr Leu Gln Gln Thr Gly Asp Ser Ile Ala Asn Glu
            275                 280                 285

Asp Ser His Asp Ser Asp His Ser Ser Glu His Ala His Leu
    290                 295                 300
```

POLYPEPTIDES COMPRISING DOMAINS OF THE GAX PROTEIN IMPLICATED IN THE REPRESSION OF TRANSCRIPTION AND/OR INTERACTION WITH OTHER PROTEINS, CORRESPONDING NUCLEIC ACIDS, AND THEIR USE

This invention pertains to the therapeutic domain. More particularly, it pertains to new therapeutic molecules and their use in the treatment of cardiovascular diseases.

BACKGROUND

Postangioplasty restenosis is a localized hyperproliferative disorder that develops following a non-surgical procedure related to atherosclerotic plaque. Thus, the treatment of an atherosclerotic lesion by angioplasty very frequently (up to 50% of the cases in some studies) results in restenosis as a result of mechanical injury to the arterial wall.

The proliferation of smooth muscle cells (SMC) in the vascular wall is a key event in the development of atherosclerosis and in restenosis after angioplasty, as well as in the failure of coronary by-pass procedures. SMCs are normally quiescent in the vascular wall, but as a result of a lesion that destroys vascular endothelium, they come into contact with blood growth factors. Unlike cardiac muscle cells and skeletal muscle cells, in response to different growth factors, SMCs can become dedifferentiated and their proliferative cycle can be set in motion again. These phenotypical changes in SMCs are the result of profound changes in the expression of numerous genes. As an example, the expression of early genes, which are involved in the proliferation of cells, such as c-fos or c-myc, is remarkably increased, although the expression of other genes with a structure such as specific smooth muscle alpha-actin, as well as certain isoforms of myosin undergo negative regulation.

Although it has been clearly established that terminal differentiation of skeletal muscle cells is regulated by so-called myogenic transcription factors, such as MyoD, very few of the factors involved in the reversible differentiation of SMCs are known as yet. Recent studies have revealed the existence of transcription factors that have a homeobox in different tissues of the cardiovascular system. Thanks to their homeobox, these factors recognize specific DNA sequences in the promoter regions of their target genes, and thus, they intervene in the regulation of cellular differentiation, proliferation or migration. One of these factors, gax (Growth-Arrest-Specific Homeobox), is expressed in different cardiovascular tissues, including the SMCs of the vascular wall. The gax gene was initially identified from rat aorta obtained from a cDNA bank. It encodes for a protein with 303 amino acids. Its sequence was characterized and its cDNA was cloned (Gorski et al., Mol. Cell. Biol. 1993, 6, 3722–3733). The human gax gene has also been cloned and sequenced (David F. Le Page et al., Genomics 1994, 24, 535–540). It encodes for a protein with 302 amino acids, which is shown below (SEQ ID NO. 16). The gax gene has certain properties that are similar to gas and Gadd genes since it seems to control the G0/G1 transition of the cell cycle. Thus, levels of gax mRNA are reduced in rat VSMC [vascular smooth muscle cells] by a factor of 10 after two hours of exposure to PDGF [platelet-derived growth factor] (Gorski et al., Mol. Cell. Biol. 1993, 6, 3722–3733). The expression of the gax gene is thus repressed during the mitogenic response of VSMC. Another characteristic of the gax gene is based on its specificity of expression. In fact, in the adult rat, the gax gene is expressed primarily in the cardiovascular system (the aorta and the heart). Northern Blotting did not determine the presence of gax mRNA in the liver, the brain, the stomach, and skeletal muscle. Moreover, the gax gene belongs to the family of homeotic genes. These genes encode for transcription factors which include consensus sequences (or homeodomains) that recognize specific regions of DNA (or homeoboxes) (review: Ghering et al., Cell, 78: 211–223, 1994). The homeodomain of rat gax protein is between amino acids 185 and 245. Interestingly, the homeotic genes identified to date are involved in the control of cell differentiation/growth during embryogenesis, which strengthens the therapeutic potential of the gax gene (review: Lawrence et Morata Cell 78: 181–189, 1994: Krumlauf, Cell 78: 191–201, 1994).

```
          0                                           5
          1                                           0
MEHPLFGCLRSPHATAQGLHPFSQSSLALHGRSDHMSYPELSTSSSSCII
                                                      1
 5                                                    0
 1                                                    0
AGYPNEEDMFASQHHRGHHHHHHHHHHHQQQQHQALQTNWHLPQMSSPPS
 1                                                    1
 0                                                    5
 1                                                    0
AARHSLCLQPDSGGPPELGSSPPVLCSNSSSLGSSTPTGAACAPGDYGRQ
 1                                                    2
 5                                                    0
 1                                                    0
ALSPAEAEKRSGGKRKSDSSDSQEGNYKSEVNSKPRKERTAFTKEQIREL
 2                                                    2
 0                                                    5
 1                                                    0
EAEFAHHNYLTRLRRYEIAVNLDLTERQVKVWFQNRRMKWKRVKGGQQGA
 2                                                    3
 5                                                    0
 1                                                    0
AAREKELVNVKKGTLLPSELSGIGAATLQQTGDSIANEDSHDSDHSSEHA
33
00
12
HL
```

One characteristic of GAX is that it undergoes a negative regulation as soon as SMCs proliferate, whether in vitro in response to growth factors, or in vivo following a lesion of the vascular wall endothelium. This repression is reversible because when the SMCs are made quiescent by deprivation in serum, in vitro, GAX expression resumes. Recent studies conducted in our laboratory showed that high-level expression of GAX in SMCs by an adenoviral vector blocks their proliferation FR 95/04234 (ST95022).

Postangioplastic restenosis following mechanical injury represents the most frequent failure factor (50% of the cases in some studies). Since SMC proliferation is a key element in this phenomenon, and since it is known that it has a regulatory role in GAX proliferation, the latter seems to be a therapeutic gene of choice for the preventive treatment of the vascular wall after angioplasty FR 95/04234(ST95022).

However, the GAX mechanism of action is still not very well documented. The target DNA sequences of the GAX homeobox still have to be identified. Moreover, as yet there have been no studies of the function of the different GAX domains. Finally, the identification of the functional partners of GAX is an important facet which will permit us to define the molecular cascade on which GAX depends or of which it is the source.

SUMMARY OF THE INVENTION

The specific advantage of this invention is to provide information regarding these points.

In the course of this study, different analytical approaches were adopted in order to identify molecules that interact with GAX, to determine the GAX domain necessary for that interaction and to investigate the importance of the different domains in the GAX function. To do this, the double-hybrid system was used to characterize proteins that interact with GAX from a human lung bank.

This approach permitted the identification of different molecules, including a particularly interesting one, the Ki antigen. The Ki antigen is a protein consisting of about 32 KDa. It was identified for the first time as a nuclear autoantigen recognized by sera from patients with lupus erythematosus (Nikaido et al. 1989, Clin. Exp. Immunol. 1990, 79, 209–214). Recent studies have revealed that Ki is overexpressed in cells during proliferation or transformed by an oncogene (Nikaido et al., 1989, Exp. Cell Res. 1989, 182, 284–289). Coimmunoprecipitation experiments (Takeushi et al. abstract 1995 Juntendo University, Tokyo, Japan) revealed that Ki exists in the form of a complex with PCNA [proliferating cell nuclear antigen], a proliferation marker (Almendral et al. 1987. Proc. Natl. Acad. Sci. USA., 84, 1575–1579).

The GAX function has also been investigated in experiments regarding the transient transfection of mammalian cells using GAX fused to a heterologic DNA-binding domain and a reporter gene system making it possible to determine the transcriptional activity of GAX after the deletion of different regions of the molecule. In this way, it was shown that GAX acts primarily as a transcription repressor. This repression activity is related, more particularly, to the first 32 amino acids of GAX. Moreover, this repressor domain is localized in GAX region (1-222) which is required for interaction with Ki in the yeast. The potential applications of the repressor characteristic of GAX and of its interaction with Ki will be explained in detail below.

A primary aspect of the invention pertains to fragments of the GAX protein that are endowed with biological properties.

Another aspect of the invention pertains to GAX domains that are involved in GAX biological activity. Notably, these may be domains involved in the interaction of GAX with other molecules or domains that are responsible for a biological activity. The invention also pertains to chimeric molecules comprising a GAX functional domain. It also pertains to the use of GAX to repress gene expression, as well as the use of compounds that inhibit GAX interaction with certain cellular partners to modulate GAX activity. It also pertains to a method for screening and/or identification of GAX cellular partners.

DETAILED DESCRIPTION OF THE INVENTION

As indicated above, the gax gene has properties that are particularly advantageous for applications of gene therapy in hyperproliferative disorders, notably restenosis or other pathologies associated with SMC proliferation. It has been demonstrated in [patent] application FR95/04234 (ST95022) that the transfer of the gax gene in vivo considerably reduces SMC proliferation, and thus, inhibits the reduction of the luminal diameter. It has also been shown in [patent] application FR 95/12871 (ST95057) that when it was expressed in tumor cells, the gax gene made it possible to oppose the process of cell transformation. These different elements demonstrate the potential of the gax gene for therapeutic maneuvers.

The present application will now describe the identification of GAX functional domains, the construction of GAX derivatives with biological activity, the identification of partners of the GAX protein and the development of methods of searching for other partners, and the identification of compounds that are capable of interacting with the activity of these partners. More specifically, the applicant has now demonstrated that the GAX protein is endowed with transcription repressor activity. It has also revealed that this activity was carried out by certain regions of the GAX protein, in particular the N-terminal region. The results presented in the examples show, in addition, that the functional domains of GAX are also involved in the interaction of GAX with a cellular protein, Ki. It is known from the literature that Ki interacts with PCNA (Takeushi et al. abstract 1995 Juntendo University, Tokyo, Japan) and that the latter is a cofactor that is necessary to DNA polymerase for DNA replication (Fukuda et al. 1995, J. Biol. Chem. 270, 22527–22534). It has been demonstrated in the examples that GAX interacts with PCNA, and thus, it is possible that it may also be involved in replicative complexes in the cell.

A primary object of the invention pertains, more particularly, to a polypeptide that is characterized in that it involves all or part of a fragment of the GAX protein which has transcription repressor activity and/or positively or negatively affects DNA replication.

More preferably, the polypeptide according to the invention includes at least residues 1 to 32 of the human GAX protein.

According to another method of embodiment, the polypeptide according to the invention includes at least residues 104 to 230 of the human GAX protein.

As particular examples of polypeptides according to the invention, we can cite polypeptides comprising fragments 1–32, 33–302 and 1–104 of the human GAX protein. The examples presented below show that such polypeptides are capable of inhibiting gene transcription, and therefore, they preserve the transcription repressor properties of GAX.

More preferably, in addition to a fragment of the GAX protein according to this invention, this polypeptide comprises a fragment of a different origin. A fragment of a different origin means a polypeptide fragment that is not obtained from the GAX protein. It may be a synthetic or artificial fragment, a protein fragment, etc. This fragment of a different origin may have different functions.

It may, for example, constitute a marker that makes it possible to detect the polypeptide, and possibly to trace it in vivo. For example, such a marker may be an epitope that is recognized by a monoclonal antibody. In this regard, different marking sequences, so-called Tag sequences, have been described in the literature and are generally used. The tag-myc sequence can be cited.

This fragment may also be a fragment that has the property of stabilizing the polypeptide. In that regard, it may be all or part of a protein that has a high plasma half-life.

Finally, it can also be a screening element, which permits the polypeptide to reach particular cell compartments more rapidly and/or more specifically. Advantageously, it is a nuclear localization signal (NLS), with the polypeptide exercising its activity principally in the cell nucleus. Different NLS signals have been described in the literature, such as for example, that for the T antigen of the SV40 virus, that of p53, etc.

The fragment of a different origin may also provide the polypeptide with an additional biological function or it may promote the activity of the repressor domain. As a particularly advantageous example, a protein domain capable of binding DNA in a specific manner can be cited. This type of chimeric molecule thus makes it possible to bind DNA in particular regions and to inhibit the transcription of genes localized in these regions. The DNA-binding domain of yeast GAL4 protein can be cited as a specific example. These structures are described in the examples. They can be used to regulate the expression of genes in yeast or of genes placed under the control of an expression signal including the GAL4 protein binding site. Other DNA protein binding domains may include, for example, Lex A, the DNA-binding domain of a nuclear receptor, such as the receptor for estrogens, or any other member of that family, etc. It can also be a peptide that permits the secretion of all or part of GAX, on the one hand, as well as targeting toward membrane receptors that permit its internalization, and thus increase the diffusability and the activity of the GAX domain by a "Bystander" type effect. In this regard, all or part of the transferrin or of the molecule fragments of the extracellular matrix can be used to recognize integrins on the surface of SMLs.

The polypeptides according to the invention are particularly advantageous on the therapeutic level and in applied research.

The claimed therapeutic activity of the polypeptides is related, more particularly, to their ability to repress transcription or to affect DNA replication, by analogy with the GAX protein, and thus to provide them with the power to regulate the expression of other proteins.

In this perspective, this invention also pertains to the use of the GAX protein or a fragment as claimed to repress gene transcription and/or to affect DNA replication positively or negatively.

Because of this behavioral analogy with the GAX protein, these fragments can advantageously be substituted in its transcription repressor function. Moreover, considering the fact that they include only all or part of the domain of the GAX protein that is involved in the repression of transcription, it is possible they will be less sensitive to the different alterations to which the GAX protein is subjected. These polypeptides, as is or as derivatives can thus manifest an increased transcription repressor characteristic compared to that of the natural GAX protein.

Their use in the identification of new GAX protein partners can also be considered. In this regard, another object of this invention is a method for screening and/or identification of polypeptides that interact with the GAX protein, or a GAX domain characterized in that it uses a polypeptide according to the invention. More preferably, this polypeptide is selected from fragments 1 to 32 and 33 to 302 of the GAX protein.

In this regard, the applicant has unexpectedly demonstrated that a domain of the GAX protein could interact specifically with another cellular protein, protein Ki. As explained previously, Ki is an autoantigen which appears during autoimmune diseases such as lupus erythematosus. It is described as a nuclear molecule whose expression increases during cellular proliferation, as well as in fibroblasts transformed by an oncogene.

We have been able to demonstrate that in yeast, the N-terminal part of GAX is necessary for interaction with Ki. The Ki recombinant protein specifically recognizes GAX that is transferred to a nitrocellulose filter from a denaturing polyacrylamide gel.

This invention also pertains specifically to a polypeptide characterized in that it is a fragment of the GAX protein that is capable of interacting with the Ki protein.

More preferably, it is the fragment 1 to 32 or 104 to 223 of the GAX protein.

The applicant has also demonstrated very unexpectedly that a domain of the GAX protein may interact specifically with the proliferation marker PCNA (Proliferating Cell Nuclear Antigen). This factor is indispensable for DNA replication and also plays a role in DNA repair phenomena.

Thus, this invention concerns a polypeptide characterized in that it is a fragment of the GAX protein that is capable of interacting with PCNA.

Moreover, Ki has been described in the literature as existing in the form of a complex with PCNA. Therefore, Ki may interact with GAX and with PCNA by forming at least a bipartite complex with one or the other of these proteins, and preferably a tripartite complex. The formation of these complexes plays an important role in the progression of the cell cycle (activation or inhibition).

Thus, this invention also pertains to a polypeptide that is characterized in that it is a fragment of the GAX protein that is capable of interacting with Ki and/or PCNA and of forming at least a bipartite, or at least a tripartite complex with these proteins.

Another object of this invention pertains to any nucleic acid that encodes for a polypeptide as defined above. It may involve sequences of natural or artificial origin, and notably genomic DNA, cDNA, mRNA, hybrid sequences or synthetic or semisynthetic sequences. This nucleic acid can be of human, animal, plant, bacterial, viral, etc. origin. It can be obtained by a technique known to those skilled in the art, and notably, by screening libraries, by chemical synthesis, or even by mixed methods including the chemical or enzymatic modification of sequences obtained by screening libraries. They can also be incorporated in vectors, such as plasmid vectors.

Advantageously, the nucleic acid according to the invention is cDNA.

The nucleic acids of the invention can be used for the production of probes or antisense molecules, which by hybridization, make it possible to detect the presence or the expression of nucleic acids encoding for polypeptides that have a repressor domain according to the invention, or to inhibit the expression of such polypeptides. With regard to probes, the latter preferably include more than 10 bases, and advantageously, from 10 to 300 bases.

The nucleic acids of the invention can be used for the expression and/or production of polypeptides in vitro, in vivo, or ex vivo, and in gene or cellular therapy manipulations.

In that regard, this invention pertains to expression cassettes containing a nucleic acid as defined above, under the control of a promoter that permits its expression.

Different promoters can be used as part of the invention. They are sequences that permit the expression of a nucleic acid in a mammalian cell.

The promoter is advantageously selected from among the functional promoters in human cells. More preferably, it is a promoter that permits the expression of a nucleic acid sequence in a hyperproliferative cell (cancer cells, restenosis, etc.). In this regard, different promoters may be used. Thus, it can be any promoter or derived sequence that stimulates or represses the transcription of a gene in a specific or non-specific, inducible or non-inducible, strong or weak manner. Notably, we can cite promoter sequences of eukaryotic or viral genes. For example, they may be promoter sequences from the genome of the target cell. Among the eukaryotic promoters, ubiquitous promoters, in particular, can be used (HPRT [hypoxanthine-guanine-phosphoribosyl transferase], PGK [phosphoglycerate kinase], alpha-actin, tubulin, DHFR [dihydrofolate reductase], etc. gene promoters), intermediary filaments promoters (promoter of GFAP [glial fibrillary acidic protein], desmin, vimentin, neurofilaments, keratin, etc. genes), promoters of therapeutic genes (for example, the promoter of MDR and CFTR [cystic fibrosis transmembrane regulator] genes, Factor VIII, ApoAI, etc.), specific tissue promoters (the promoter of the pyruvate kinase gene, villin, intestinal fatty acids binding protein, smooth muscle alpha-actin, etc.), specific cell promoters of types of dividing cells, such as cancer cells or even promoters that respond to a stimulus (steroid hormones receptor, retinoic acid receptor, glucocorticoid receptor, etc.) or so-called inducible [promoters]. In like manner, they may be promoter sequences from a virus genome, such as for example, promoters of adenovirus E1A and MLP genes, the early CMV [cytomegalovirus] promoter, or even the LTR [long terminal repeat] promoter of the RSV [respiratory synctial virus], etc. Moreover, these promoter regions may be modified by the addition of activating or regulating sequences, or those that permit a tissue-specific or majority expression.

This invention now provides new therapeutic agents which, due to their ability to repress transcription, make it possible to intervene in numerous cellular dysfunctions. With this objective, the nucleic acids or cassettes according to the invention may be injected as is into the site to be treated, or incubated directly with the cells to be destroyed or treated. In fact, naked nucleic acids that might penetrate the cells without a particular vector have been described. Nevertheless, according to this invention, it is preferable to use an administration vector which improves (i) the efficacy of cellular penetration, (ii) targeting and (iii) extra-and intracellular stability.

In one particularly preferable embodiment of the invention, the nucleic acid or the cassette is incorporated into an expression vector. The vector used may be of chemical (liposome, nanoparticle, peptide complex, lipids or cationic polymers, etc.), viral (retrovirus, Adenovirus, herpes virus, AAV [adeno-associated virus], vaccine virus, etc.) or plasmid origin.

The use of viral vectors is based on the natural transfection properties of the virus. For example, it is possible to use adenoviruses, the herpes virus, retroviruses, and adeno-associated viruses. These vectors have proven to be particularly efficient on the transfection level. In that regard, a preferred object according to the invention is based on a defective recombinant retrovirus, the genome of which includes a nucleic acid as defined above. Another particular object of the invention is based on a defective recombinant adenovirus, of which the genome includes a nucleic acid as defined above.

The vector according to the invention may also be a non-viral agent that is capable of promoting the transfer and expression of nucleic acids into eukaryotic cells. Chemical or biochemical, and synthetic or natural vectors represent an interesting alternative to natural viruses, particularly for reasons of convenience and safety, and also because there is no theoretical limit regarding the size of the DNA to be transfected. These synthetic vectors have two principal functions, to compress the nucleic acid to be transfected and to promote its cellular fixation, as well as its passage through the plasma membrane, and if necessary, the two nuclear membranes. To compensate for the polyanionic nature of the nucleic acids, all non-viral vectors have polycationic charges.

The nucleic acid or the vector used in this invention can be formulated with a view to topical, oral, parenteral, intranasal, intravenous, intramuscular, subcutaneous, intraocular, transdermal, etc. administration. Preferably, the nucleic acid or the vector is used in an injectable form. Therefore, it can be mixed with any vehicle that is pharmaceutically acceptable for an injectable formulation, notably for a direct injection into the site to be treated. In particular, it may be in the form of sterile, isotonic solutions or dry compositions, notably freeze-dried compositions, which after the addition of sterilized water or physiological serum, as the case may be, constitute injectable solutes. The doses of the nucleic acid used may be adapted in terms of the different parameters, and notably, as a function of the gene, the vector, the method of administration used, the pathology in question, or even the desired duration of the treatment.

The invention also pertains to any pharmaceutical composition comprising at least a nucleic acid as defined above.

It also pertains to any pharmaceutical composition comprising at least a vector as defined above.

Because of their antiproliferative properties, the pharmaceutical compositions according to the invention are particularly well-suited for the treatment of hyperproliferative disorders, such as notably, cancers and restenosis. Thus, this invention provides a particularly efficacious method for the destruction of cells, notably hyperproliferative cells. It is, therefore, applicable to the destruction of tumor cells or to the smooth muscle cells of the vascular wall (restenosis). It is very particularly suited to the treatment of cancers. As an example, we can cite adenocarcinomas of the colon, thyroid cancers, carcinoma of the lungs, myeloid leukemias, colorectal cancers, breast cancer, lung cancer, stomach cancers, esophageal cancers, B lymphomas, ovarian cancers, bladder cancers, glioblastomas, hepatocarcinomas, cancers of bone, skin, pancreas or even kidney and prostate cancers, cancers of the esophagus, cancers of the larynx, cancers of the head and neck, HPV [human papilloma virus] positive anogenital cancers, EBV [Epstein-Barr virus] positive nasopharynx cancers, etc.

Moreover, this invention also extends to any use of compounds that inhibit the activity of the Ki protein and/or of PCNA to inhibit the proliferation of smooth muscle cells.

This invention also pertains to the use of compounds according to the invention for the formation of a bi- or tripartite complex with Ki and/or PCNA proteins to affect the progression of the cell cycle positively or negatively.

This invention will be more completely described using the following examples and figures, which should be regarded as illustrative and non-limiting.

BRIEF DESCRIPTION OF THE DRAWINGS

FIG. 3A Coomassie blue

FIG. 3B Far Western Blotting

FIG. 4B Determination of CAT enzymatic activity in cellular extracts after transfection with expression vectors incorporating ER, GAL VP16 and ER-GAL VP16, respectively.

FIG. 6A) Without the ER activator

FIG. 6B) in the presence of the ER activator.

MATERIALS AND METHODS

A) MATERIALS

Figure 1:
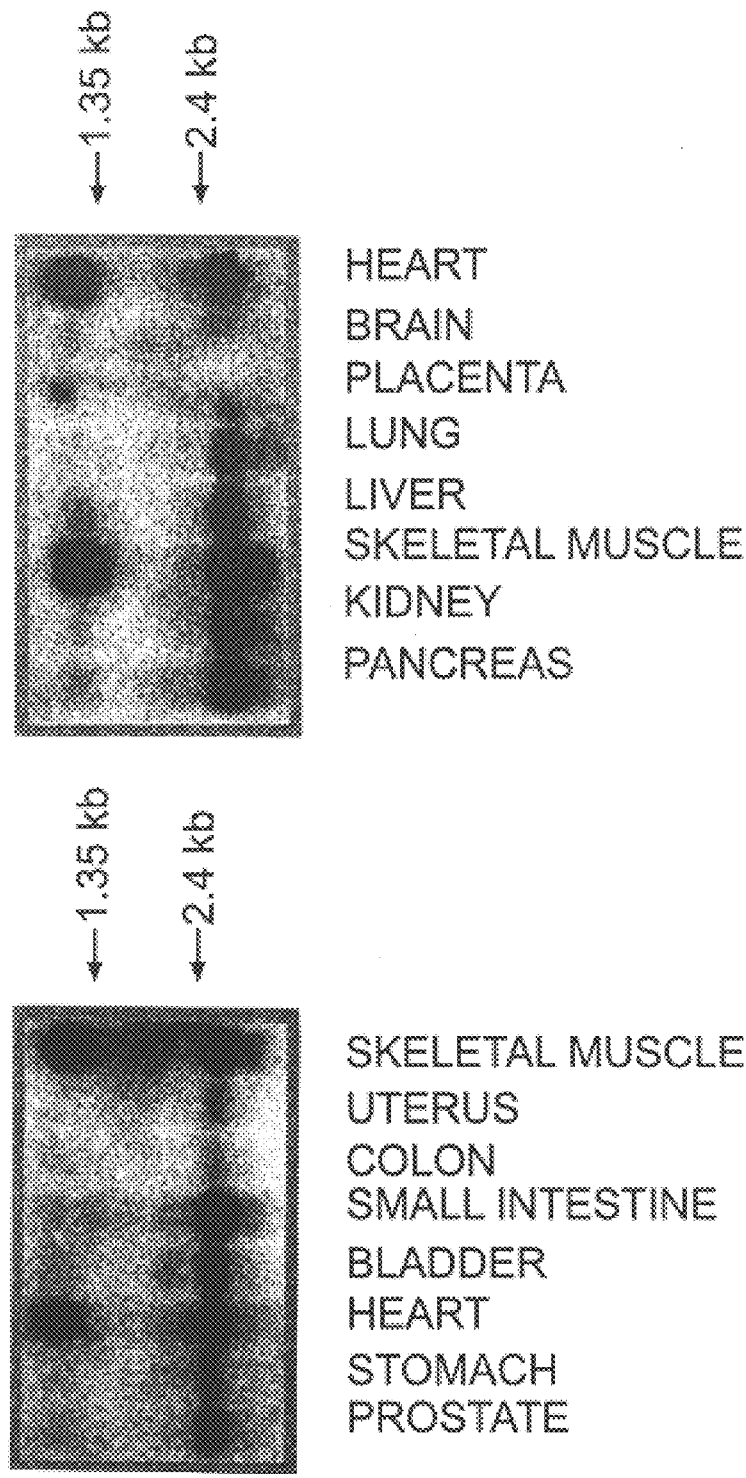
FIG. 1: Northern blotting analysis of the expression of the Ki protein from mRNA extracted from different tissues.

1) Yeast Strain Used:

Strain YCM79 of the genus *S. cerevisiae* (MATa, ura3-52, his3-200, ade2-101, lys2-801, trp1-901, leu2-3,112, can1, gal4-542, gal80-538, met16::URA3-pGAL1/10-LacZ, HIS3::GAL7BLE) was used as the screening tool from the lung fusion bank by the two hybrid system.

It is cultivated on the following culture media:
Complete YPD Medium: Yeast extract (10 g/l) (Difco)
Bactopeptone (20 g/l) (Difco)
Glucose (20 g/l) (Merck)
This medium was solidified by the addition of 20 g/l of agar (Difco)
Minimum YNB [yeast nitrogen base] medium:
Yeast Nitrogen Base (without amino acids) (6.7 g/l) (Difco)
Glucose (20 g/l) (Merck)
This medium was solidified by the addition of 20 g/l of agar (Difco).

To permit the growth of auxotrophic yeasts on this medium, the amino acids or nitrogen bases on which they are dependent must be added to it, at the rate of 50 mg/ml.

2) Bacteria Strains Used:

Strain TG1 of *Escherichia coli*, genotype supE, hsdD5, thi, D(lac-proAB), F'[tra D36 pro A$^+$B$^+$ lacI$^q$ lac ZDM15] was employed as the means of isolation and amplification of the recombinant plasmids used.

The *E. coli* bacteria used for the production of recombinant proteins are BL-21 obtained from Pharmacia. *E. coli*. They have the genotype F$^-$ ompT hsdS$_b$ ($r_b$_m$_b$$^-$) gal dcm (DE3).

BL-21 is a strain of choice for the production of recombinant proteins because it contains no protease and its membrane is fragile and easily ruptured by simple sonication. *E. coli* BL-21 has a system for the repression of T7 RNA polymerase. This repression can be increased by IPTG [isopropyl thiogalactose] which permits control of genes placed downstream from the T7 RNA polymerase binding site. The bacteria are cultured in 2 ml of the LB [laked blood] medium (NaCl 5 g/l, Tryptone 10 g/l, Yeast extract 5 g/l) in an agitator at 37° C. overnight. 1 ml of this preculture is cultured again in 50 ml of the 2×YT medium (NaCl 5 g/l, Tryptone 16 g/l, Yeast extract 10 g/l) at 37° C. until the bacteria reach an optical density (OD) of 0.4 at 600 nm (exponential growth phase). The bacterial culture is cooled on ice. They are centrifuged at 3300 rpm for 20 minutes.

The *E. coli* bacteria, which are competent for the production of recombinant proteins are prepared by the calcium chloride method. To do this, the bacteria are dissolved in 5 ml of 0.1 M CaCl$_2$ (1/10 of the culture). They are centrifuged again at 3300 rpm for 10 minutes. They are dissolved again in 1 ml of 0.1 M CaCl$_2$ containing 17.5% glycerol. They are aliquoted and stored at –80° C.

3) Plasmids Used:

The following plasmids are used:

The vectors from the pGBT and pAS series (Clontech) of shuttle plasmids originate from [both] bacterial and yeast replication, which means that a large number of copies can be replicated in these two microorganisms. These plasmids contain a multiple cloning site situated downstream from the sequence encoding for the GAL4 DNA-binding domain and upstream from a terminator to form a fusion protein. They also contain the TRP1 gene of *S. cerevisiae*, which complements yeasts which have the trp1 genotype, so that they can be selected on a minimum medium that does not contain tryptophan. These vectors carry the ampicillin-resistant gene, which permits the selection of bacteria that possess them on a medium that contains ampicillin.

Vectors from the pGAD series (Clontech) are vectors that permit the expression in yeast of fusion proteins between the GAL4 transactivator domain and a protein of interest or [one that is] encoded for cDNA obtained from a lung bank, inserted at the level of an EcoRI Xho1 site.

Vectors from the pET29 series (Novagen) are vectors that permit the expression of recombinant proteins in coli fused with tagS.

Vectors from the pGEX series (Pharmacia) are vectors that permit the expression of recombinant proteins in coli fused with Glutathione S-Transferase (GST).

Vectors from the Bluescript series (Strata gene) are vectors that permit cloning like the pIC series (J. Lawrence Marsh et al. Gene, 1984, 32, 481–485) and the pMTL series (Steve P. Chambers et al., Gene, 1998, 68, 139–149).

Plasmid pGEX-2T-hGAX is the plasmid used for the transformation of *E. coli* B-2. This plasmid was obtained from the pGEX-2T plasmid and was furnished by Doctor K. Walsh of St. Elizabeth's Medical Center in Boston. The base plasmid pGEX-2T (Pharmacia) permits the production of the GAX protein fused with Glutathione-S-Transferase (GST), a protein which has a strong affinity for Glutathione. The GST-GAX fusion will facilitate the purification of GAX by affinity on agarose beads coupled with Glutathione. Moreover, there is a splice site by thrombin which subsequently permits the chimera to be divided between GST and GAX. cDNA hGAX is inserted under the control of the tac hybrid promoter and the lac operator. By attaching itself to the lac operator, the lacI repressor prevents RNA polymerase from advancing. This repression is increased by an analog of lactose, isopropyl-β-D-thiogalactoside (IPTG) which is associated with lacI. The lacI-IPTG complex can no longer bind to the lac operator, and thus, there is no longer any obstacle to the RNA polymerase.

4) Ki Protein

Production and Purification

We cloned the gene of the Ki protein fused to an myc epitope in the pET-29 plasmid (Novagen) from the pGAD plasmid contained in the yeast. The pET-29 plasmid produced the protein fused to the epitope called S-Tag, which permits the purification of KI by affinity on agarose beads coupled with S-protein. The SmycKI chimera is controlled by promoter T7 and the lac operator. The BL-21 s are transformed by the pET-29-mycKI plasmid. As for the GST-GAX protein, they are cultured until they reach an OD of 0.7 at 600 nm. Then, the expression of SmycKI is induced by 0.1 mM of IPTG and by the T7 RNA polymerase produced by the BL-21s. The bacteria are sonicated. The supernatant is then purified by the following method. The purification of SmycKI takes place by affinity on agarose beads coupled with S-protein. The method is the same as for GST-GAX except that the resin is washed in a solution. containing 20 mM of Tris pH 7.5, 0.15 M NaCI and 0.1% Triton X-100. Elution and dialysis are the same as for GST-GAX.

B) METHODS

The classic methods used in molecular biology are well known to those skilled in the art and are fully described in the literature [Maniatis T. et coll., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

1) The Double-hybrid System

This system is a method of cloning by in vivo interaction in Saccharomyces cerevisiae, and its principle is based on the modular structure of the transcription factor of the GAL4 (7) yeast. The GAL4 transcription activator has two independent domains which have different functions. The DNA-binding domain (GALDB for GAL DNA-Binding) permits GAL4 to bind to a specific DNA sequence at the level of the promoter region of a gene. GAL4 is then found sterically near the transcription machinery, and thanks to its transactivator domain (GALTA), it increases the frequency with which the transcription is initiated on the adjacent gene, probably due to interactions with RNA polymerase or associated proteins. The principle of the double hybrid system consists of separately fusing GALDB and GALTA to two different proteins X and Y, which reconstitute an active transcription complex when they interact.

2) Screening Yeasts by the PCR (Polymerase Chain Reaction) Technique

The screening takes place directly on the yeasts. Each yeast colony is dissolved in 10 µl of water containing 0.08% Tween 20. The Tween is a nonionic detergent which increases yeast lysis during the first heating stage at 95° C. For subsequent stages, Tween 20 acts as a protective agent of the Taq DNA polymerase. The yeast suspension is filled to a final volume of 20 µl containing the following final quantities or concentrations: 10 picomoles of primer 1, 10 picomoles of primer 2, 1 unit of Taq DNA polymerase, 75 mM of Tris pH 9, 20 mM of $(NH_4)2SO_4$, 0.01% Tween 20, 2.5 mM of $MgCl_2$ and 125 µM of each of 4 deoxyribonucleotides (dATP, dTTP, dGTP and dCTP). At the end of the PCR, a fraction of the mixture is analyzed on an agarose gel. Thus, it is possible to determine for a given pair of primers and for each yeast clone, whether a previously identified DNA sequence is involved.

3) Preparation of Plasmid DNAs

Large quantities of DNA are prepared using the Promega DNA rapid preparation Kit.

Small quantities of DNA are prepared in the following manner: bacteria containing the plasmid are cultured for at least 4 hours in 2 ml of LB medium in an agitating shaker. They are then centrifuged for 3 minutes at 14,000 rpm in Eppendorf tubes, and then the residue is suspended in 100 µl of solution I (50 mM of glucose, 25 mM of Tris HCl buffer pH 8, 10 mM of EDTA pH 8), lyzed by 200 µl of solution II (0.2 M NaOH, 1% SDS). The lysis solution is then neutralized with 150 µl of solution III (3 M potassium acetate, 11.5% (v/v) glacial acetic acid). After the tubes are agitated to obtain a flaky precipitate, 150 µl of a phenol/chloroform mixture (50% phenol and 50% chloroform saturated in water) is added, and the entire mixture is agitated for 30 seconds. The aqueous phase containing the DNA is recovered after centrifugation for 2 minutes at 14,000 rpm. The DNA is then precipitated by adding 0.5 volume of isopropanol, then centrifuged for 5 minutes at 14,000 rpm and air-dried, and finally taken up in 20 µl of TE RNAse (a solution of Tris 10 mM HCl and 1 mM EDTA with 50 µg/ml of RNAse).

4) Synthesis and Enzymatic Amplification of DNA or PCR (Polymerase Chain Reaction)

PCR reactions are carried out in a total volume of 100 µl in the presence of the DNA matrix, of NTP (0.2 mM), PCR buffer (Tris HCl pH 8.5 10 mM, $MgCl_2$ 1 mM, KCl 5 mM, gelatin 0.01%), 0.5 µg of each of the oligonucleotides and 2.5 IU of Ampli Taq DNA polymerase (Perkin Elmer) with or without formamide (5%). The mixture is covered with 2 drops of paraffin oil to limit evaporation of the sample. The instrument used is the "Crocodile II" from Appligene. We used a matrix denaturation temperature of 90° C., an oligo-nucleotide hybridization temperature in the matrix of 5 to 10 degrees below the separation temperature of the oligonucleotides and an enzyme-assisted elongation temperature of 72° C.

The fragments obtained by PCR which are used for cloning are routinely resequenced after they are cloned to verify the absence of any mutation that may appear during amplification.

Oligodeoxynucleotides are synthesized chemically according to the phosphoramidites method using β-cyanoethyl protector groups (Sinha 1984). After synthesis, the protector groups are eliminated by treatment with ammonia and two precipitations in butanol to purify and concentrate the oligodeoxynucleotides (Sawadogo, 1991). The DNA concentration is determined by measuring the optical density at 260 nm.

5) Ligations

All ligation reactions are carried out at +14° C. overnight in a total volume of 10 µl in the presence of 100 to 200 ng of vector, 0.5 to 2 µg of insert, 40 IU of the T4 DNA ligase enzyme (Biolabs) and a ligation buffer (Tris-HCl 50 mM pH 7.8; MgCl$_2$ 10 mM; DTT 10 mM; ATP 1 mM). The negative control is consists of the ligature of the vector in the absence of insert.

Filling the prominent 5' ends is carried out, if necessary, before ligature by the Klenow fragment of E. coli DNA polymerase I (Biolabs) according to the supplier's specifications. Destruction of the prominent 3' ends is carried out in the presence of the DNA Polymerase of the T4 phage (Biolabs) used according to the manufacturer's recommendations.

6) Bacteria Transformation

Bacteria are transformed by a plasmid according to the following protocol: The total ligature volume (10 μl) is used to transform TG1 bacteria that have been rendered competent by the method of Chung et al. (PNAS, 1988 86, 2172–2175).

TG1 bacteria are cultured in a liquid LB medium for several hours in a shaking oven at 37° C., until an OD of 0.6 at 600 nm is obtained. The medium is then centrifuged at 6,000 rpm for 10 minutes. The bacteria are rendered competent by taking up the bacterial residue with a volume of TSB (LB medium+100 g/l of PEG 4,000, 5% DMSO, 10 mM MgCl$_2$, 10 mM of MgSO$_4$) which represents 1/10 of the volume of the initial culture medium. After incubation at 4° C. for 30 to 60 minutes, 200 μl of bacteria are placed in contact with the ligation products for 15 minutes on ice. After the addition of 200 μl of LB, the bacteria are incubated for 30 minutes at 37° C. and then spread on a LB+ampicillin medium.

7) DNA Separation and Extraction

DNAs are separated as a function of size by electrophoresis. To do this, different gels are used depending on the size of the fragments to be separated:

1% agarose gel (Gibco BRL) in a TBE buffer (Tris base 90 mM; Borate 90 mM; EDTA 2 mM) to separate large DNA fragments (larger than 500 bp [base pairs])

2% NuSieve agarose gel (FMC Bioproducts) in a TBE buffer to separate small fragments (less than 500 bp).

All migration on agarose gel or on polyacrylamide gel takes place in a TBE buffer and in the presence of a molecular weight marker (1 Kb ladder, Gibco BRL). The DNA is mixed with 1/10 of the volume of blue marker (200 g/l of Ficoll, 0.5 g/l of bromophenol blue, 50 mM of EDTA) before being deposited on the gel. After migration at 100 volts and staining with ethidium bromide (concentration 0.5 μg/ml of gel), the bands are visualized under the UV lamp.

The DNA is extracted from the agarose gel band by electroelution as follows: The piece of gel that contains the DNA fragment is cut with a scalpel and placed in a dialysis column sealed by two clips and containing 100 to 500 μl of TBE. The mixture is placed in an electrophoresis tank where it is subjected to an electric field of 100 volts. After being removed from the gel, the DNA is then purified by two extractions with phenol/chloroform followed by two extractions with chloroform, then precipitated in the presence of 0.3 M sodium acetate and 2.5 volumes of absolute ethyl alcohol. After centrifugation (5 minutes at 14,000 rpm), the DNA residue is dried and then taken up with 20 μl of water.

8) Fluorescent Sequencing of Plasmid DNAs

Sequencing takes place according to Sanger's method using 4 dideoxyribonucleotides with a different fluorescent marker. The incorporation of one of these dideoxyribonucleotides produces a stop in the replication by the Taq polymerase of the DNA to be sequenced. This reaction will produce different sizes of DNA fragments, all terminated at the 3' end by one of the 4 dideoxyribonucleotides.

One μg of a plasmid and 4 picomoles of a primer are added to 9.5 μl of a "premix" supplied by Applied Biosystems called Prism©. The total volume should be 20 μl to carry out a Polymerase Chain Reaction for 25 cycles broken down into a denaturation step at 96° C. for 30 seconds, a hybridization step at 50° C. for 15 seconds and an extension step at 60° C. for 4 minutes.

The DNA fragments, which are obtained after amplification, are purified on an exclusion column (Chromaspin-39 from Clontech); and they are then dried in the Speed Vac. The entire mixture is taken up with 5 μl of a mixture consisting of 24 μl of EDTA (50 mM) and 120 μl of deionized formamide. After denaturation at 96° C. for 3 minutes, 3 to 5 μl are deposited on an electrophoresis gel. The different DNA fragments are separated according to size and are then passed before a DNA 370 Sequencer laser reader (Applied Biosystems) where the different fluorescences will be detected.

9) Preparation of Plasmids from the Lung Bank (Clontech®).

The lung cDNA fusion bank is sold in the form of bacteria. This bank is obtained from cloning, at the EcoRI-XhoI site of the pGAD424 plasmid (Materials and Methods), with cDNA corresponding to total RNAs from human lung cells.

After the titer of the bank has been verified, 2 μl of bacteria from the lung fusion bank, which were previously placed in 8 ml of LB, are spread in a non-confluent manner on a solid medium in order to preserve the representativity of this bank. Thus, we spread [the bacteria on] 16 770 cm$^2$ dishes containing a LB+ampicillin medium. The colonies that appeared in each dish were taken up with 30 ml of liquid LB+ampicillin. The suspensions obtained were then placed in an Erlen and incubated in a shaker at 37° C. for 3 hours. The DNA was then extracted from these strains by the Maxiprep technique. The DNA concentration will be determined at 260 nm.

10) Transformation of Yeast by a Plasmid

Yeasts that have previously been cultured in 100 ml of liquid medium are collected after centrifugation at 3,000 rpm for 3 minutes and suspended in 1 ml of sterile water. After centrifugation at 3,000 rpm for 3 minutes, the cellular residue is resuspended in 1 ml of sterile water and then centrifuged again. This operation is repeated once again in order to eliminate all traces of the culture medium. The yeasts are then taken up by 1 ml of transformation solution I (LiAc 0.1M, Tris-HCl pH 7.5 10 mM, EDTA 1 mM), then centrifuged at 3000 rpm for 3 minutes. The cellular residue is taken up again in 1 ml of transformation solution I. 50 μl of this yeast suspension is placed in the presence of 50 μg of salmon sperm DNA and 1 to 5 μg of plasmid DNA. 300 μl of transformation solution II (LiAc 0.1 M, Tris-HCl pH 7.5 10 mM, EDTA 1 mM in 40% PEG4000) is then added, and the mixture is then incubated at 28° C. for 30 minutes. A thermal shock is then applied to the transformation mixture in a water bath at 40° C. for 15 minutes, and then the mixture is centrifuged at 15,000 rpm for 1 minute in order to collect the cellular residue. This residue is taken up in 200 μl of water, then spread on a minimum agar mixture that contains no amino acids, corresponding to the markers carried by the transforming plasmid. The yeasts are then cultured for 72 hours at 28° C.

In the particular case of the transformation of yeast by the lung cDNA bank, the procedure is as follows:

The yeast used contains plasmid pGAL4DB-GAX expressing the GAX protein in fused form at the GAL4 to DNA binding domain. It is cultured in 250 ml of a minimum YPG medium at 28° C. under agitation to obtain a density of $10^7$ cells/ml. The cells are collected by centrifuging at 300 rpm for 10 minutes and taken up in 250 ml of water. After another centrifugation, the cellular residue is taken up in 100 ml of water and centrifuged again. The residue is then taken up in 10 ml of transformation solution I and incubated for 1 hour at 28° C. under agitation. After centrifugation, the cells are again taken up in 2.5 ml of transformation solution I, 100 µl of the lung cDNA bank and 20 ml of transformation solution II, then incubated for 1 hour at 28° C. under agitation. A thermal shock is applied to this transformation mixture at 42° C. for 20 minutes. Centrifugation (3000 rpm for 5 minutes) is repeated 3 times immediately afterwards, and each time the residue is taken up with 10 ml of sterile water. The third time, the residue is taken up with 2.5 ml of PBS [phosphate-buffered saline]. This eliminates PEG, which is toxic to the cells. 2.4 ml of this suspension is used to seed 250 ml of minimum medium containing the amino acids His, Lys, Met and bases Ura and Ade, and this is cultured overnight in a shaker at 28° C. The remaining 100 µl of this suspension is used to verify the efficacy of the transformation; in order to do this, dilutions of $10^{-2}$, $10^{-3}$ and $10^{-4}$ of this suspension were prepared. The overnight culture is centrifuged (3,000 rpm for 5 minutes) and immediately washed with sterile water twice. The residue is then taken up in 2.5 ml of water. 2.4 ml of this is increased to a volume of 10 ml in sterile water and used to seed 10 dishes of 435 cm² containing a YNB+Lys+Met+His+Ade medium and incubated for 3 days. The remaining 100 µl is used to perform the same operations as those used to determine the rate of transformation, in order to determine the rate of amplification of the number of colonies during an overnight culture.

11) Preparation of Yeast DNA (genomic and plasmid)

The amount of an average loopful of a yeast clone is placed in 200 µl of a TELT solution (Triton X100 2%, SDS 1%, NaCl 100 Mm, Tris pH 8 10 mM, EDTA 1 mM), in the presence of 3 g of glass beads with a diameter of 4 µm and 200 µl of phenol/chloroform. This mixture is vortexed for 15 minutes, then centrifuged for 2 minutes at 14,000 rpm. The supernatant is collected without removing the protein cake and the DNA contained in this phase is precipitated with 2.5 volumes of absolute ethyl alcohol. After centrifugation for 2 minutes at 14,000 rpm, the DNA residue is dried and taken up in 20 µl of TE-RNAse. This DNA solution, which represents a mixture of genomic and plasmid DNA, is used directly to transform bacteria. Only plasmid DNA is capable of replicating in bacteria and can be analyzed by the miniprep technique.

12) β-galactosidase Activity Test

A sheet of nitrocellulose is first deposited on the Petri dish containing the individualized yeast clones. As a result of an adsorption phenomenon, a faithful image of the clone placement is obtained. This sheet is then immersed in liquid nitrogen for 30 seconds in order for the yeasts to rupture, and thus, release β-galactosidase activity. After thawing, the nitrocellulose sheet is deposited, colonies upward, in another Petri dish containing a Whatman paper previously impregnated with 1.5 ml of PBS solution ($Na_2HPO_4$ 60 mM, $NaH_2PO_4$ 40 mM, KCl 10 mM, $MgSO_4$ 1 mM, pH 7) and 10 to 30 µl of X-Gal (5-bromo-4-chloro-3-indoyl-b-D-galactoside) at the rate of 50 mg/ml in N,N-dimethylformamide. The dish is then placed in an oven at 37° C. with the cover closed to prevent drying. The time needed for the blue coloration to appear may be extremely variable, from a few minutes to several hours. This test should always be done in the presence of a positive control for which the interaction is known and which turns blue rapidly.

13) Construction of expression vectors and reporter gene a) Expression Vectors

Estrogen receptor (ER) cDNA is obtained by reverse transcription (RT) using a commercial kit (first strand cDNA synthesis Kit from Pharmacia), from total RNA extracted from mouse uterus, followed by amplification by PCR. We used a specific pair of primers, hybridizing, in 5' with the first 20 ER nucleotides and introducing an EcoRI site immediately downstream from the first codon (540 -gagcgaattc<u>ATG</u>ACCATGACCCTTCACAC SEQ ID No. 6, with the nucleotides in italics representing the EcoR I site and the ones in underlined capital letters [representing] the first codon), from the 3' side the return primer begins at the ER stop codon while also introducing an EcoR I site (5'-gagcgaattc <u>ACT</u>GATCGTGTTGGGGAAGC SEQ ID No. 7, with the nucleotides in italics representing the EcoR I site and those in underlined capital letters the stop codon). The PCR fragment obtained was purified, digested by EcoRI, and then cloned at the same site in the pcDNA 3 expression vector (Invitrogen). This vector is called pCMV-ER. The different deletion mutants of GAX fused in the DNA-binding domain of GAL4 (pCMV-GALDB/GAX, see Example 9) were also cloned in the pcDNA 3 vector.

b) Reporter Gene

The reporter gene was constructed according to the strategy described by Martinez et al (Martinez et al. 1991, *Mol. Cell. Biol.* 11, 2937–2945) except that the cloning vector used is pG5CAT (Clontech, CAT=Chloramphenicol Acetyl Transferase). We synthesized a double-strand oligonucleotide (below) containing two specific sites (in bold-face type), one recognized by the DNA-binding domain of GAL4 (Gal-17mer, Carey et al. 1989, *J. Mol. Biol.* 209, 423–432) and the other is a consensus sequence of the "Estrogen Responsive Element" (<u>ERE</u>, Beato M. 1989, *Cell* 56, 335–344), which binds the receptor to the estrogens. This adapter oligonucleotide has a protrusive XhoI site at 5' and an XbaI site at 3' which permitted cloning of pG5CAT in the Xho I and Xba I sites.

```
tcgagAGGTCATATTGACCTaagcttCGGGTCGGAGTACTGTCCTCCGACTGCcatatgt SEQ ID No. 8
    cTCCAGTATAACTGGAttcgaaGCCCAGCCTCATGACAGGAGGCTGACGgtatacagatc SEQ ID No. 9
XhoI       ERE                       Gal-17mer              Xba I
```

Figure 4A:
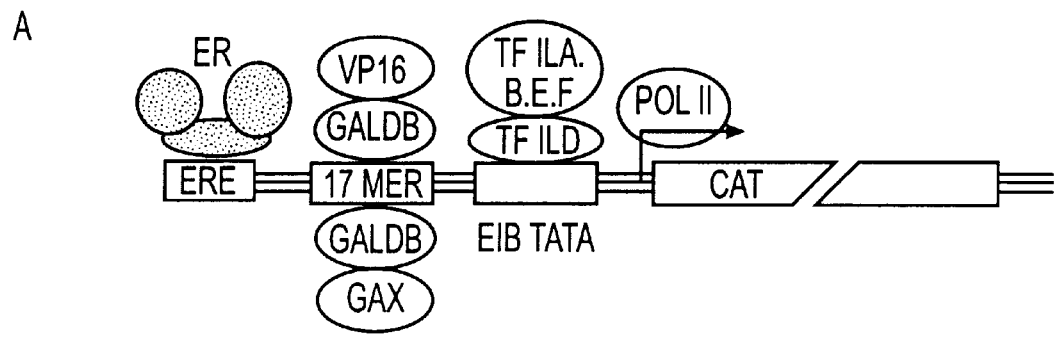
FIGS. 4A–4B Representation of the construction of the Reporter gene expressing bacterial chloramphinicol actyl transferase (CAT) under the control of an artificial promoter.
Figure 4B:
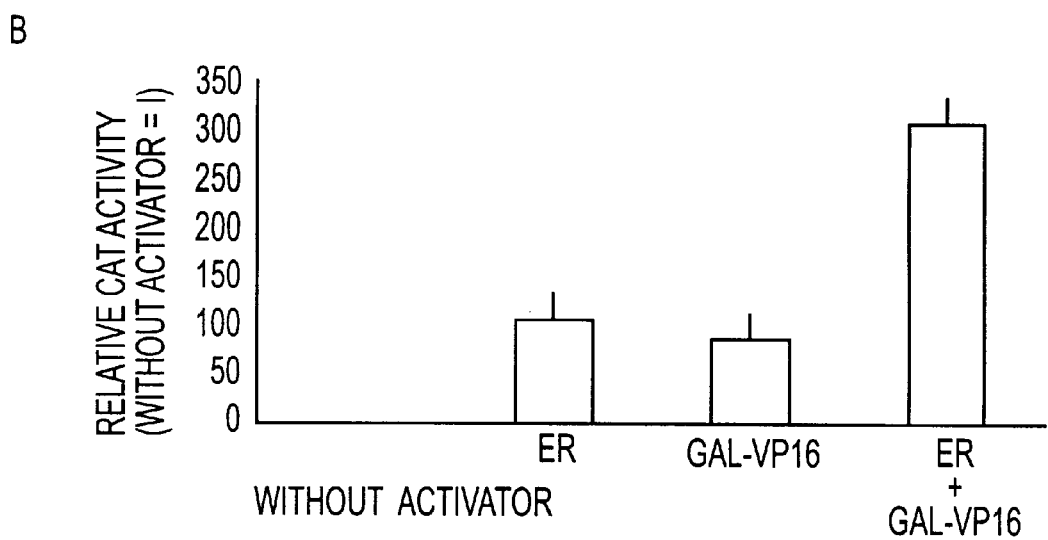
Figure 5:
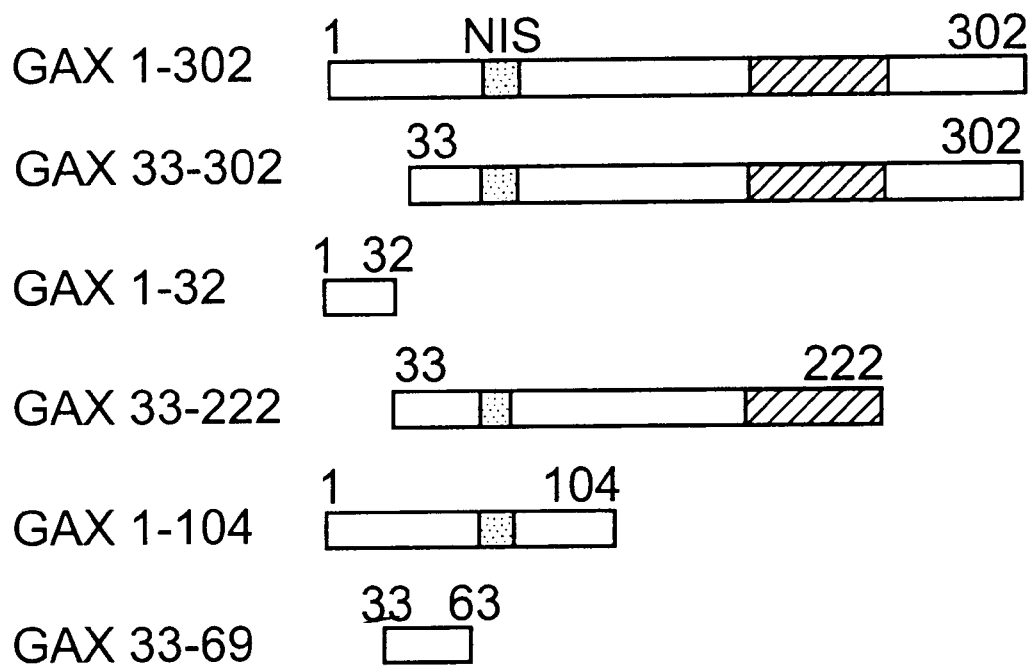
FIG. 5: Comparison of the constructions of the different GAX deletion mutants in relation to the complete GAX protein 1-302.

The principle of this reporter gene (pEREG1CAT, FIG. 4, Example 11)) is based on the fact that ER is a transcription activator, which in the case of murine ER, has a constituent activity that increases in response to its natural ligand, estradiol 17β. This system was used by Martinez et al. to study the synergism between ER and a second transcription factor, NF1, the transcription activator domain of which was fused to the DNA-binding domain of the GAL4 yeast protein (GALDB). Thus, this reporter makes it possible to determine the transcription rate that is due to only one or the other of the transcription factors, or of their cooperation without interference due to endogenous molecules. This system, therefore, makes it possible to study the transcription activity of all or part of the GAX protein fused to GALDB (FIGS. 5 and 6 and Examples 12 and 13).

A plasmid expressing the luciferase gene under the control of the SMC promoter (pCMV[SMC]-Luc) was constructed. This structure was obtained after cloning a PCR fragment (flanked at 5' and 3' by a BamHI site) containing the SMC promoter of the pcDNA3 vector (Invitrogen), in the BglII site of the pGL3-Basic vector (Promega). This plasmid will be used as the internal standard in all of the following transient transfection experiments.

14) Transient Cotransfection Experiments

All of the studies were conducted in murine embryonic fibroblasts NIH3T3 (ATCC). These cells were routinely maintained in DMEM (GIBCO) supplemented with 100 U/ml of penicillin (GIBCO), 100 μg/ml of streptomycin (GIBCO), 2 mM L-glutamine (GIBCO) and 10% fetal calf serum (FCS, GIBCO). This medium will be designated by the abbreviation DMEM-GPS/FCS.

For the transient transfection experiments, the NIH-3T3 are seeded at a density of 100,000 cells per well of a 24-well culture plate (Falcon), in a volume of 1 ml of DMEM-GPS/FCS. Sixteen to twenty hours later, after fixation and spreading of the cells, the cells are washed with 0.5 ml of DMEM-GPS (without FCS), then placed in 0.5 ml of DMEM-GPS. 50 μl of a transfection mixture are then added per culture well. This mixture is obtained as in summary Table 3 below.

TABLE 3

|  | 1* | 2* | 3* | 4* |
|---|---|---|---|---|
| pCMV-Luc | 50 ng | 50 ng | 50 ng | 5 ng |
| pEREG1CAT* | 650 ng | 650 ng | 650 ng | 650 ng |
| pCMV-ER | — | 150 ng | — ng | 150 ng |
| pCMV-GALDB/GAX | — | — | 150 ng | 150 ng |
| pCDNA3** | 300 ng | — | — | — |
| Lipofectamine*** | 8 μg | 8 μg | 8 μg | 8 μg |
| H₂O qsp | 50 μl | 50 μl | 50 μl | 50 μl |

The cells are placed in contact with the different transfection mixtures for 4 hours at 37° C. under standard culture conditions. The DMEM-GPS, with the transfection mixture, is then replaced with 1 ml of DMEM-GPS/FCS, and the cell culture is then continued for 24 hours. Each transfection is carried out on a minimum of 4 wells.

At the end of the 24-hour period, the cells are washed with 0.5 ml of Dulbecco's PBS (GIBCO), then collected in 0.5 ml of a 0.2% trypsin solution in PBS (GIBCO). The trypsin is neutralized with 10 μl of FCS. This cellular suspension is centrifuged for 2 minutes at 10,000 g, the supernatant is extracted, and the cells are then resuspended in 150 μl of Tris-HCl 0.25 M at pH 7.8. 50 μl of this suspension is used to determine the luciferase activity according to the "Luciferase Assay System" kit (Promega) using the LUMAT LB 9501 Luminometer (EG&G Berthold).

The cytosolic proteins of the cells in the remaining 150 μl are extracted by 5 freezing/thawing cycles (liquid nitrogen/37° C.). These extracts, which are standardized in relation to the luciferase activity, are then used to determine the CAT activity according to the method previously described by Gorman et al (Gorman et al. 1982, Mol. Cell. Biol. 5, 1044–1051).

15) In vitro Interaction Between Ki and GAX Proteins

This is carried out using the Far-Western Blotting method.

While Western Blotting consists of an electrophoretic separation of proteins on a denaturing gel followed by electrotransfer of the proteins on a nitrocellulose membrane and direct or indirect immunodetection, Far-Western Blotting is a Western-Blotting [technique] to which is added a protein-protein interaction step between a target immobilized on the nitrocellulose membrane and a factor in solution.

a) Electrophoresis

The samples are heated for 10 minutes at 95° C. in a denaturation buffer for proteins containing 50 mM of Tris pH 6.8, 2% SDS (Sodium Dodecyl Sulfate), 10% glycerol, 300 mM of b-mercaptocthanol and 0.1% of bromophenol blue. Ten ml of the samples are deposited on Tris-Glycine 14% Acrylamide (Tris-Glycine Gels, Novex). Migration takes place for 1 hour at a constant voltage of 10 V in a protein separation buffer (35 mM of SDS, 1.92 M of Glycine and 85 mM of Tris pH 8.3). The molecular weight of the proteins will be determined by migration in parallel with a colored and transferable molecular weight standard (MultiMark™ Multi-Colored Standard, Novex). This gel is duplicated so that one of the two can be colored in parallel with Coomassie blue (Methanol 30%, water 60%, acetic acid 10%, Coomassie blue 0.1%). Coloration [takes] 1 hour. Decoloration is carried out, over several hours, with the decoloration solution (Methanol 30%, Acetic acid 10%, water 60%) being changed several times. The limit of detection of this method is 50 ng of proteins. This colored gel thus allows us to visualize all of the proteins that are deposited. The other gel is used for the "Far-Western Blotting".

b) Semi-dry Transfer on a Nitrocellulose Membrane

The nitrocellulose membrane (Hybond C from Amersham) and the gel are placed between 3 thicknesses of Whatman paper that was previously immersed in the transfer buffer (Glycine 150 mM, Tris 25 mM, Methanol 20%, water qsp 1 liter, pH 8.3). The transfer takes place over 40 minutes at 2.5 mA/cm² of gel (Milliblot™-Graphite Electroblotter II, Millipore).

c) Protein-protein Interaction

The membrane is saturated for 30 minutes under agitation and at room temperature in PBS containing 5% (w/v) of powdered skim milk (Gloria) and 0.2% (v/v) of Tween 20. Next, it is immersed for 1 hour under agitation and at room temperature in 5 ml of PBS containing 5% (w/v) of powdered skim milk (Gloria), 0.2% (v/v) of Tween 20 and 75 μg of KI. When the incubation is completed, the membrane is washed 3 times for 10 minutes in PBS containing 0.2% (v/v) of Tween 20. In order to visualize the interaction between the GST-GAX immobilized on the nitrocellulose membrane and mycKi, the latter is revealed as for GST-GAX using a mouse monoclonal antibody directed against the myc epitope (Santa Cruz) and a rabbit polyclonal antibody, coupled with peroxidase, directed against mouse IgG (Nordic Immunology).

EXAMPLES

Example 1
Construction of a Vector to Permit the Expression of a Fusion Protein Between GAX and the GAS4 DNA Binding Domain Screening a bank using the double-hybrid system requires the GAX protein to be fused to the DNA-binding domain of the GAL4 transactivating protein. The expression of this fusion protein takes place via the pGBT10 vector (cf materials and methods), into which we introduced, in the same reading frame as the sequence corresponding to the GAL4 DNA-binding domain (GAL4DB), a fragment encoding for all or part of the GAX protein. A particular fragment includes the EcoR1-Sal 1 fragment derived from phGAX, which is inserted at the EcoR1-Sal 1 site of pGBT 10 to produce plasmid pCM 199.

The structure was sequenced which makes it possible to verify that the GAX protein is actually in the same open reading phase as that of the fragment corresponding to GAL4DB.

Example 2
Screening the Lung Fusion Bank.

Screening a fusion bank makes it possible to identify clones that produce fused proteins in the GAL4 transactivator domain, which may interact with the GAX protein or with domains of the latter. This interaction makes it possible to reconstitute a transactivator, which will then be capable of inducing the expression of reporter genes URA3, BLE and LacZ in the YCM79 strain.

To perform the screening, we selected a fusion bank prepared from cDNA obtained from human lung. Since this bank was supplied to us in the form of bacteria, the plasmid DNA from the bank was first purified.

2.1) Preparation of Plasmid DNA from a Fusion Bank

The plasmid DNA from the lung cDNA bank was extracted according to the Clontech® protocol (see materials and methods §10). During this preparation, it was important to preserve the representativity of the bank, that is, to preserve the number of constituent independent plasmids, which number $7.10^6$ plasmids.

In order to prevent the loss of plasmids from the bank during this preparation, the batch of plasmid DNA that we prepared was obtained from a number of isolated bacterial colonies corresponding to a little more than 3 times those represented by the bank or $25.10^6$ colonies.

2.2) Transformation by Lung Bank and Selection by the Beta-galactosidase Activity Test During screening, the probability that each independent plasmid from the fusion bank is present in at least one yeast at the same time as the GAL4DB-GAX plasmid must be preserved. To preserve this probability, it is important to have good yeast transformation efficacy. For this, we chose a yeast transformation protocol that provides an efficacy of $10^5$ transformed cells per µg of DNA. Moreover, since cotransformation of the yeast by two different plasmids reduces this efficacy, we preferred to use a yeast that was previously transformed by the pGAL4DB-GAX plasmid.

This yeast strain was transformed by 100 µg of plasmid DNA from the fusion bank. This amount of DNA permitted us to obtain, after estimating (see materials and methods) 4.2 $10^7$ transformed cells, which is a larger number than the number of independent plasmids that make up the bank. According to this result, we believe that nearly all of the plasmids from the bank were used to transform the yeast. Transformed cells that were capable of reconstituting a functional GAL4 transactivator were selected on a YNB+ Lys+Met+His+Ade medium. At the end of this selection, 190 clones with a Ura+and βGal+phenotype were obtained.

Example 3
Identification of Selected Plasmid Inserts: Detection of Interaction with Ki The plasmids were extracted from the yeast, introduced into the bacteria, and then prepared as described in the materials and methods section. The sequencing was carried out from the complementary oligonucleotide CTATTCGAT-GATGAAGATACCCC (SEQ ID No. 1) of the GAL4TA region near the insertion site of the lung cDNA bank, at 52 bp from the EcoRI site.

The comparison of the sequences with the sequences contained in the GENBank and EMBL (European Molecular Biology Lab) data banks showed that one of the plasmids thus identified includes a cDNA that is identical to the Ki factor, identified in patients with lupus as an autoantigen. This plasmid was christened pCM282. When this plasmid is transformed in the yeast with pCM199, it is entirely capable of activating the reporter genes of the latter as shown in Table 1 below.

This Table also shows that the activation is specific, which indicates that Ki is capable of interacting specifically with GAX.

TABLE 1

| Vectors | Beta-gal activity |
| --- | --- |
| pCM199 + Pgad424 | 0 |
| pCM199 + pCM282 | + |
| pGBT10 + pCM282 | 0 |
| pGBT10 + pGAD424- | 0 |

Example 4
Construction of Vectors that Permit the Expression in Yeast of a Fusion Protein Between Different Deletants of GAX and the DNA Binding Domain of GAL4

This example describes the construction of vectors encoding for different variants of the Gax protein, that can be used to determine the structure/function of that protein, and notably, can reveal the active domains and the domains that are responsible for interaction with the Ki protein.

The deletion of 153 C-terminal amino acids is obtained by digesting the plasmid pCM199 by Eag1-Sal1; the small fragment is then eliminated, the ends are made blunt by Klenow treatment and religated. The plasmid obtained is called pCM238. It encodes for a protein that includes GAX residues 1-104.

The total digestion of pCM199 by Bg12 and Sal1, and then religation of the vector after Klenow treatment preserves the first 32 GAX amino acids. The plasmid obtained is called pCM244. It encodes for a protein including GAX residues 1-32.

Total digestion of pCM199 by Bg12 and Sal1 permits the isolation of a fragment of approximately 270 bp and 572 bp. The first fragment is cloned in pGBT11 at the Bamh1-Sal1 site to obtain plasmid pCM245 which permits the fusion of 79 C-ter amino acids with GAL4DB. The second fragment is cloned in pGBT10 at the Bamh1 site to obtain pCM246 which permits the fusion of amino acids 33 to 222 with GAL4DB.

Plasmid pCM280 is obtained by digesting pCM246 by Dra3 and pst1. After treatment with polymerase T4, the plasmid closes on itself again. It encodes for a protein that includes GAX residues 33–63.

Plasmid pCM199 is digested by Nde1 and Pst1. The insert is cloned in plasmid pAS1 to yield plasmid pCM301. This plasmid permits the expression of the GAX protein deleted from these first 32 amino acids fused to GAL4DB. It encodes for a protein that includes GAX residues 33–302.

The structure of the fused protein expressed by these different vectors is represented in FIG. 5.

Example 5
Localization of the Region of GAX Interaction with Ki

Yeast strain yCM79 is transformed by the different vectors described in Examples 1 and 4 at the same time as pCM282 or pGAD424. Beta-gal activity is revealed as described in materials and methods. The results obtained are presented in Table 2 below.

TABLE 2

| Vectors | Beta-gal activity |
| --- | --- |
| pCM199 + pGAD424 | 0 |
| pCM199 + pCM282 | + |
| pCM238 + pGAD424 | 0 |
| pCM238 + pCM282 | 0 |
| pCM244 + pGAD424 | 0 |
| PCM244 + pCM282 | 0 |
| pCM245 + pGAD424 | 0 |
| pCM245 + pCM282 | 0 |
| pCM246 + pGAD424 | 0 |
| pCM246 + pCM282 | 0 |
| pCM280 + pGAD424 | + |
| pCM280 + pCM282 | + |
| pGBT10 + pCM282 | 0 |
| pCM301 + pCM282 | 0 |

These results reveal the GAX region that interacts with the Ki factor (Table 2). In fact, since the activity of the regions is lost when they are absent, we can conclude that they are necessary for the interaction, but not sufficient. Thus, regions 1 to 32 and 104 to 223, seem to be important for interaction with Ki. The fact that pCM238 does not give a positive signal in Beta-gal, suggests that there is a C-Term region 104–302 of Gax that is necessary for the interaction in yeast.

Example 6
mRNA Expression Profile in Different Tissues and Nuclear Localization of Protein Expressed Temporarily:

In order to identify GAX partners, we transformed our double hybrid yeast strain, which already possesses the plasmid that permits the expression of GAL-GAX fusion (1-302) as bait, by a lung cDNA bank fused to GAL4 TA, which was available in the laboratory (Example 2). Before amplification, we were able to obtain more than 41 million independent clones, and only 190 clones in which the 3 selection genes (i.e. the URA3 gene, the LacZ gene and the BLE gene) were expressed. Nine cDNAs encoding for different proteins could be identified among these 190 clones. We are more particularly interested in the one that encodes for the Ki antigen.

The Ki gene seems to be ubiquitous, as suggested by the Northern blotting analysis (FIG. 1) of its expression from mRNA extracted from different tissues (human Multiple Tissue Northern Blots, Clontech) which reveal an mRNA with approximately 3 kb [kilobases]. The presence of a form of mRNA that undergoes a different maturation (1.4 kb) can be observed in the heart and skeletal muscles.

The construction of a vector that permits the expression of the Ki protein fused to the tag HA in mammalian cells was carried out in the following manner: the Nco1-Xho1 fragment of the pCM282 Plasmid is inserted in the pAS1 plasmid at the Nco1-Xho1 sites to obtain plasmid pCM322. Then the EcoR1-Dra1 fragment of the pCM322 plasmid is inserted in the pCDNA3 expression vector at the EcoR1-EcoRV sites. After the plasmid is obtained, pCM323 permits the expression of the ki protein fused to tag HA in the mammalian cells.

Figure 2:
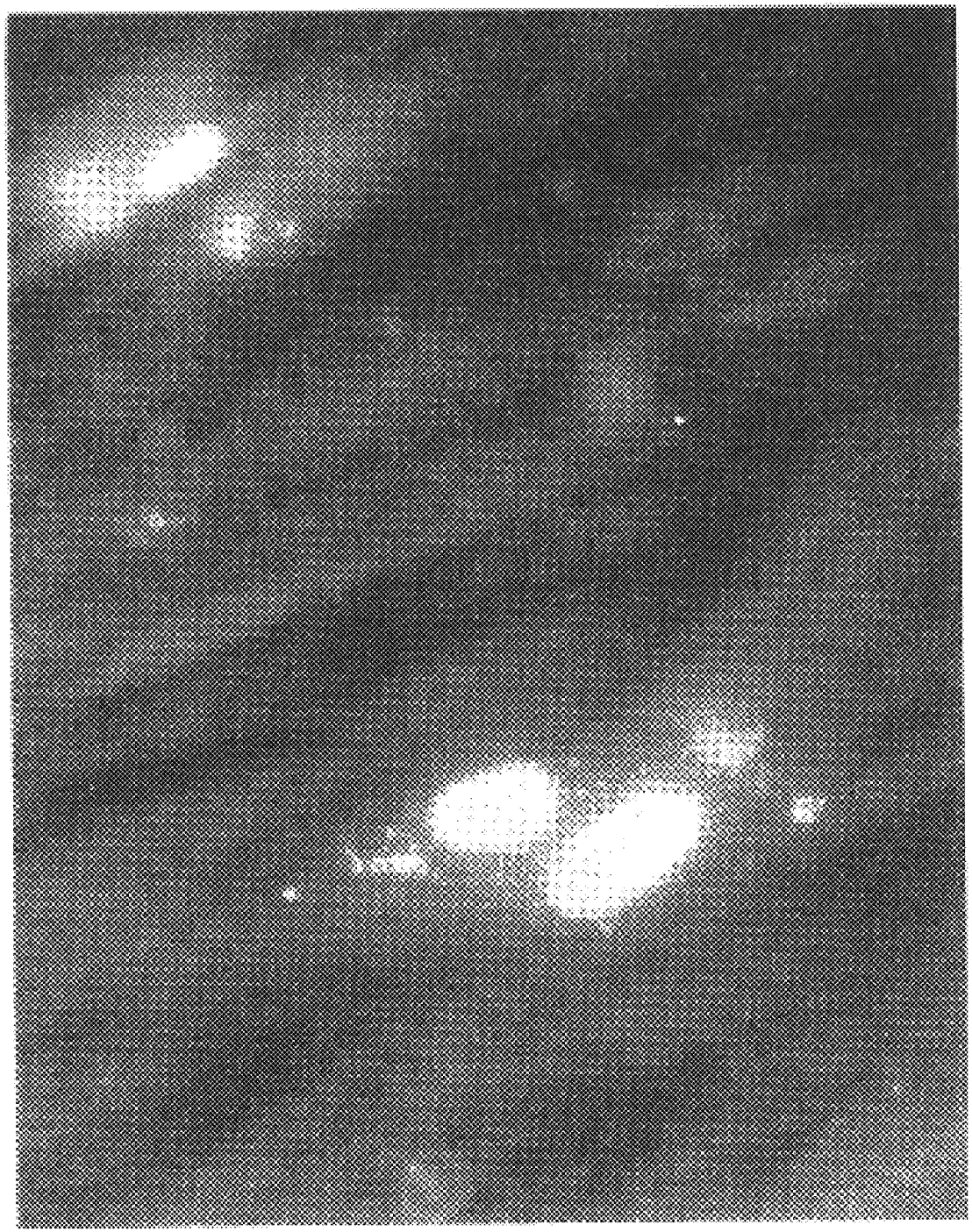
FIG. 2: Nuclear localization of KiHA in cells transfected by the immunofluorescence method.

Indirect immunofluorescence shows that KiHA has a nuclear localization in cells transfected by this chimera (FIG. 2).

Example 7
Expression and Purification of Protein Ki Fused to tag S and Tag myc.

The following oligos are hybridized together, phosphorylated, and then ligated with pET29B that has previously been digested by Nco1.

CATCAAGCTTATGGAGCAGAAGCT-GATCTCCGAGGAGGACCTGCAGCTTC (SEQ ID No. 2) and

CATGGATCCACGTGCAGGTCCTCCTCG-GAGATCAGCTTCTGCTCCATAAGCTT (SEQ ID No. 3)

The plasmid obtained is named pCM320. The gene encoding for the Ki protein is amplified by PCR with oligos CGCGGATCCCATGGCCTCGTTGCTG (SEQ ID No.4) and GTAGAGCTCGAGTCAGTACAGAGTCTCTGC (SEQ ID No. 5). The fragment obtained is digested by Bamh1 Xho1, then introduced, after ligation to the bamH1-Xho1 sites of the pBCks plasmid to yield plasmid pCM305. The latter is then digested by Bamh1 and Xho1. The insert released is bound to the Bamh1 and Xho1 site of pCM320 to produce plasmid pCM321. The expression and purification of the recombinant protein are carried out according to the manufacturer's instructions (Novagen) from pCM321.

Example 8
Expression and Purification of the GAX Protein Fused to GST

BL-21 colonies transformed by the plasmid pGEX-2T-h-GAX are precultured in 30 ml of LB with ampicillin (50 µg/ml) at 37° C. overnight. Five ml of this preculture are cultured in 500 ml of LB with ampicillin at 37° C. until an optical density of 0.7 at 600 nm is obtained. The expression of GST-GAX is induced by 0.1 mM of IPTG for 2 hours at 30° C. The culture is centrifuged at 6,000 rpm for 10 minutes. The bacteria residues are dissolved in 10 ml of cold PBS then distributed in 10 Eppendorf tubes. The bacterial proteins are extracted by sonication for 10 minutes with 12-second cycles and pauses of 24 seconds followed by centrifugation at 15,000 rpm for 15 minutes. The supernatants are pooled, and they constitute the soluble fraction that will be used for purification. The remaining residues represent the insoluble fraction.

GAX is purified by affinity of GST on agarose beads combined with Glutathione. The supernatant obtained after sonication of the bacteria is incubated with the resin for one hour on a rotary agitator at room temperature. Then, the resin on which the protein is bound is centrifuged at 1000 rpm for 10 minutes. After the supernatant is eliminated, the resin is washed 3 times with 50 ml of PBS containing 1% Triton X-100 for 20 minutes on a rotary agitator. GST-GAX can be eluted from the resin by guanidine thiocyanate. Elution is carried out by 1.5 times the volume of resin of 2M guanidine thiocyante, 20 mM of Tris pH 7.5, 0.15 M NaCl and 0.1% Triton X-100 on a rotary agitator for 30 minutes. The eluate is dialyzed against PBS overnight to eliminate the guanidine thiocyanate. The protein is stored in PBS at 4° C. A cocktail of an equal quantity of protease inhibitors (Leupeptin 1 mg/ml, Pepstatin 1 mg/ml, Aprotinin 1 mg/ml, Benzamidine 500 mM) is added to the protein preparation at [the rate of] 1/200.

Example 9

Interaction In Vitro Between Ki and GAX Proteins

In order to investigate the interaction of GAX and Ki in vitro, we produced two chimeric recombinant proteins in Escherichia coli. GST-GAX was purified on a resin combined with glutathione by means of the catalytic site of glutathione S-transferase (GST); with SmycKi carrying an myc epitope and the S epitope permitting the purification of a resin combined with the protein S.

Figure 3:
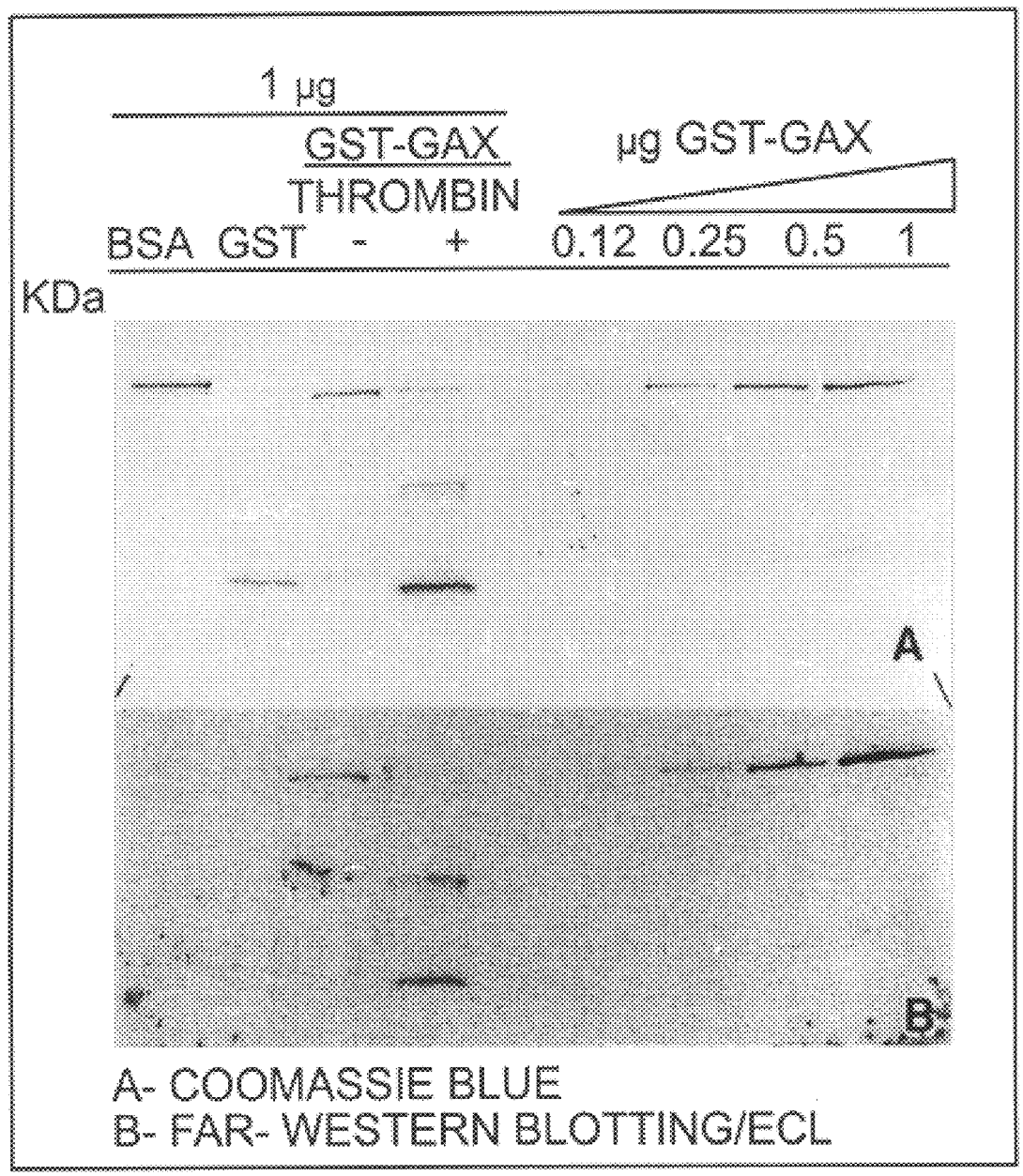
FIGS. 3A–3B: In vitro interaction between Ki and GAX proteins

The indicated quantities of bovine albumin, and the GST protein or GST-GAX after digestion by thrombin (site created between GST and GAX), as well as increasing quantities of GST-GAX were separated on a denaturing polyacrylamide gel, then stained with Coomassie blue (FIG. 3A).

The proteins were transferred to a nitrocellulose membrane from a gel identical to that in A. The membrane was subsequently incubated in the presence of SmycKi, in a solution containing a mouse monoclonal antibody directed against the myc (Santa Cruz) epitope, and finally, in a solution for the detection of the anti-myc antibody.

Our results clearly show that Ki specifically recognizes GST-GAX in a dose-dependent manner, while no reaction was observed with bovine albumin or GST. Note that after digestion by thrombin, Ki always interacts with GAX (FIG. 3B).

Example 10

Construction of Vectors that Permit the Expression in Mammalian Cells of a Fusion Protein Between Different GAX Deletants and the DNA-binding Domain of GAL4.

10.1 Construction of Plasmid Vectors

Plasmids pCM199 and pCM301 are digested by HindIII. The inserts are cloned in the correct orientation in pcDNA3 (invitrogen) at the HindIII site to yield plasmids pCM291 and pCM327, respectively, thus permitting the expression of fusions in mammalian cells.

Plasmids pCM238, pCM244, pCM301, pCM246 and pCM280 are digested by HindIII and NaeI. The inserts are cloned in the correct orientation in pCDNA3 (invitrogen) at the HindIII-EcoRV site to yield plasmids pCM292, pCM326, pCM327, pCM294 and pCM295, respectively, thus permitting the expression of fusions in mammalian cells.

10.2 Construction of Viral Vectors

According to one particular embodiment, the invention is based on the construction and use of viral vectors that permit the in vivo transfer and expression of nucleic acids as defined above.

More particularly, with regard to the adenovirus, different serotypes, the structure and properties of which vary only slightly, have been characterized. Among these serotypes, according to this invention, it is preferable to use type 2 or 5 human adenoviruses (Ad2 or Ad5) or adenoviruses of animal origin (see patent application WO94/26914). Among adenoviruses of animal origin that can be used according to this invention, we can cite adenoviruses of canine, bovine and murine origin (for example: Mav1, Beard et al, Virology 75 (1990) 81) and ovine, porcine, avian or even simian (for example: SAV) origin. Preferably, the adenovirus of animal origin is a canine adenovirus, and more preferably a CAV2 adenovirus [Manhattan strain or A 26/61 (ATCC VR-800) for example]. According to the invention, it is preferable to use adenoviruses of human or canine or mixed origin.

Preferably, the defective adenoviruses of the invention include ITRs a sequence that permits encapsidation and a nucleic acid according to the invention. Still more preferably, in the genome of the adenoviruses of the invention, at least the E1 region is non-functional. The viral gene considered may be rendered non-functional by any method known to those skilled in the art, and notably, by total suppression, substitution, partial deletion, or addition of one or more bases in the gene or genes considered. Such modifications may be obtained in vitro (on isolated DNA) or in situ, for example, by means of genetic engineering techniques, or even by treatment with mutagenic agents. Other regions may also be modified, and notably region E3 (WO95/02697), E2 (WO94/28938), E4 (WO94/28152, WO94/12649, WO95/02697) and L5 (WO95/02697). According to a preferred embodiment, the adenovirus according to the invention includes a deletion in regions E1 and E4. According to another preferred embodiment, it includes a deletion in region E1 at the level of which are inserted region E4 and the nucleic sequence of the invention (cf FR94 13355). In the virus of the invention, the deletion in region E1 preferably extends from nucleotides 455 to 3329 on the Ad5 adenovirus sequence.

Defective recombinant adenoviruses according to the invention can be prepared by any method known to those skilled in the art (Levrero et al., gene 101 (1991) 195, EP 185,573; Graham, EMBO J. 3 (1984) 2917). In particular, they can be prepared by homologous recombination between an adenovirus and a plasmid that includes, among other things, a nucleic sequence or a combination of the nucleic sequences of the invention. The homologous recombination takes place after cotransfection of said adenovirus and plasmid in an appropriate cell line. The cell line used should preferably (i) be transformable by said elements, and (ii) include sequences that are capable of complementing the part of the genome of the defective adenovirus, preferably in integrated form to avoid the risks of recombination. As an example, we can cite human embryonic kidney line 293 (Graham et al., J. Gen. Virol. 36 (1977) 59) which contains, notably, integrated in its genome, the left part of the genome of an Ad5 adenovirus (12%) or lines that are capable of complementing the E1 and E4 functions as described notably in Patent Applications No. WO94/26914 and WO95/02697 or in Yeh et al., J. Virol. 70 (1996) 559. Then, the adenoviruses which are multiplied are recovered and purified according to classic molecular biology techniques.

With regard to adeno-associated viruses (AAV), these are relatively small DNA viruses, which are integrated in the genome of the cells that they infect, in a stable and site-specific manner. They are capable of infecting a broad spectrum of cells, without inducing any effect on cell growth, morphology or differentiation. Moreover, they do not seem to be involved in human pathologies. The AAV genome has been cloned, sequenced and characterized. It includes approximately 4700 bases and at each end it includes a inverted terminal repeat (ITR) of approximately 145 bases, which is the origin of replication for the virus. The rest of the genome is divided into 2 essential regions having the encapsidation functions: the left part of the genome, which contains the rep gene involved in viral replication and the expression of viral genes; and the right part of the genome, which contains the cap gene encoding for the capsid proteins of the virus.

The use of vectors derived from AAVs to transfer genes in vitro and in vivo has been described in the literature (see notably WO 91/18088; WO 93/09239; U.S. Pat. Nos. 4,797,398, U.S. Pat. No. 5,139,941 and EP 488,528). These patent applications describe different structures derived from AAV, in which the rep and/or cap genes are deleted and replaced by a gene of interest, and their use for the in vitro (on cultured cells) or in vivo (directly into an organism) transfer of said gene of interest. The defective recombinant AAVs according to the invention can be prepared by co-transfection, into a cell line infected by a human helper virus (for example, an adenovirus), from a plasmid containing a nucleic sequence or a combination of nucleic sequences of the invention flanked by two inverted terminal repeats (ITR) of AAV, and a plasmid carrying the encapsidation genes (rep and cap genes) of AAV. For example, cell line 293 can be used. Other production systems are described, for example, in patent applications WO95/14771; WO95/13365; WO95/13392 or WO95/06743. The recombinant AAVs that are produced are then purified by classic techniques.

With regard to herpes viruses and retroviruses, the construction of recombinant vectors has been fully described in the literature: see notably Breakfield et al., New Biologist 3 (1991) 203; EP 453,242, EP 178,220, Bernstein et al. Genet. Eng. 7 (1985) 235; McCormick, BioTechnology 3 (1985) 689, etc. In particular, retroviruses are integrative viruses, which selectively infect cells during division. Thus, they constitute vectors of interest for cancer applications. The retrovirus genome includes essentially two LTR [long terminal repeats], an encapsidation sequence and three coding regions (gag, pol and env). Recombinant vectors derived from retroviruses and from gag, pol and env genes are generally completely or partly deleted and replaced by a heterologic nucleic acid sequence of interest. These vectors may be obtained from different types of retroviruses such as notably, the MoMuLV ("Moloney murine leukemia virus"; also designated MoMLV), the MSV ("Moloney murine sarcoma virus:), the HaSV ("Harvey sarcoma virus"); the SNV ("spleen necrosis virus"); the RSV ("Rous sarcoma virus") or the Friend virus. In order to construct recombinant retroviruses according to the invention that include a nucleic nucleic [sic] sequence or a combination of nucleic sequences according to the invention, a plasmid including notable LTRs, the encapsidation sequence and the so-called nucleic sequence is constructed, then used to transfect a so-called encapsidation cell line, capable of supplying in trans the retroviral functions that are missing in the plasmid. Generally, encapsidation lines are thus capable of expressing the gag, pol and env genes. Such encapsidation lines have been described in the prior art, and notably the PA317 line (U.S. Pat. No. 4,861,719); the PsiCRIP line (WO90/02806) and the GP+envAm-12 line (WO89/07150). Moreover, recombinant retroviruses can include modifications in LTRs to suppress transcription activity, as well as extended encapsidation sequences that include part of the gag gene (Bender et al., J. Virol. 61 (1987) 1639). The recombinant retroviruses that are produced are then purified using classic techniques.

10.3 Chemical Vectors

The nucleic acids or plasmid expression vectors described in the previous examples can be administered as is in vivo or ex vivo. In fact, it has been demonstrated that naked nucleic acids can transfect cells. However, to improve the transfer efficacy, according to the invention, it is preferable to use a transfer vector. This may be a viral vector (Example 9.2) or a synthetic transfection agent.

Among the synthetic vectors that have been developed, according to the invention, it is preferable to use cationic polymers of the polylysine type (LKLK)n, (LKKL)n, SEQ ID NO:14 (SEQ ID NO:15 LKKL)n, (PCT/FR/00098) polyethylene imine (WO96/02655) and DEAE-dextran or even cationic or lipofectant lipids. They have the property of condensing DNA and promoting its association with the cell membrane. Among the latter, can be cited lipopolyamines (lipofectamine, transfectam, etc.) and different cationic or neutral lipids (DOTMA, DOGS, DOPE, etc.), as well as peptides of nuclear origin. In addition, the concept of targeted transfection has been developed, mediated by a receptor, which takes advantage of the principle of condensing DNA via the cationic polymer while directing the fixation of the complex to the membrane by chemical coupling between the cationic polymer and the ligand of a membrane receptor that is present on the surface of the cell type that is to be grafted. Targeting the transferrin or insulin receptor or the receptor of asialoglycoproteins of hepatocytes has been described. The preparation of a composition according to the invention using this type of chemical vector can be carried out according to any technique known to those skilled in the art, generally simply by placing the different components in contact with one another.

Example 11

Development of a Method for Studying the Transcription Activity of GAX

We used a transient transfection system to study the transcription activity related to GALDB-GAX fusions, as well as their effect on transcription activators, such as estrogen receptors (ER) or the acid activation domain of protein VP16 or the *Herpes simplex* virus fused to GALDB. In order to quantify the transcription activity of each one or of the combination of several factors, we constructed a target gene (Reporter) which expresses bacterial chloramphenicol acetyl transferase (CAT) under the control of an artificial promoter. This promoter contains a TATA box, obtained from the EIB gene of adenovirus Ad2 (E1B TATA), upstream from the initiation site of the CAT gene transcription (FIG. 4A). A TBP protein of the TFIID complex, recognizes the TATA box and positions the preinitiation complex (TFIID+TFII A,B,E,F) which recruits type II RNA polymerase (PolII), which will initiate the transcription of the CAT gene. Upstream from this basic promoter, we inserted a GALDB binding site (17mer) which will be recognized by the GALDB-GAX or GALDB-VP16 chimera. Upstream from the 17 mer, we also cloned an estrogen response element (ERE) on which ER binds to activate transcription. This reporter will permit us to study the different simplified combinations; activation or repression of transcription will be represented by a change in the quantity of CAT in a cell. The determination of the CAT enzymatic activity in the cellular extracts after transfection is used to measure the transcription effect.

ER and GAL4-VP16 are extremely strong transcription activators. CAT activity is increased more than 100-fold by ER and approximately 85-fold by GAL4-VP16. The coexpression of ER and GAL4-VP16 results in CAT activity that is more than 300 times greater than that of the unactivated reporter and greater than the sum of the two activators expressed individually. This suggests that in spite of steric hindrance, ER and GAL4-VP16 can occupy and activate the same promoter (FIG. 4B).

Example 12
Study of the Transcription Activity of GALDB-GAX Fusions and Identification of a Transcription Repressor Domain The GAX gene encodes for a protein with 302 amino acids in man. The primary structure of this protein has different domains whose function is as yet unknown. GAX belongs to a family of so-called homeobox (HOMEOBOX) genes. The homeobox is needed for recognition and binding of these proteins to the specific DNA sequences present on the promoter of the target genes, whose expression they control. No DNA sequence recognized by GAX has been identified as yet. GAX has a region rich in Histidine (HIS) residues in its N-terminal section, and its function is unknown.

To understand the function of GAX different regions of the human GAX gene have been deleted to produced truncated proteins in both their N-terminal and C-tenninal sections; the numbers indicate the position of the first and last amino acid of each deletion mutant compared to the entire GAX 1-302 (FIG. 5). Since we do not know which DNA sequence is naturally recognized by GAX, we created chimera between the different deletion mutants and a heterologous DNA-binding domain (fused to their N-terminal section) obtained from the yeast transcription factor GAL4 (GALDB). Expression vectors were constructed for the transient expression of the different chimera in cultured mammalian cells.

The different GAL-GAX chimera were expressed alone or in the presence of ER to study their effect on basic transcription or on the transcription activity of ER, respectively.

Figure 6A:
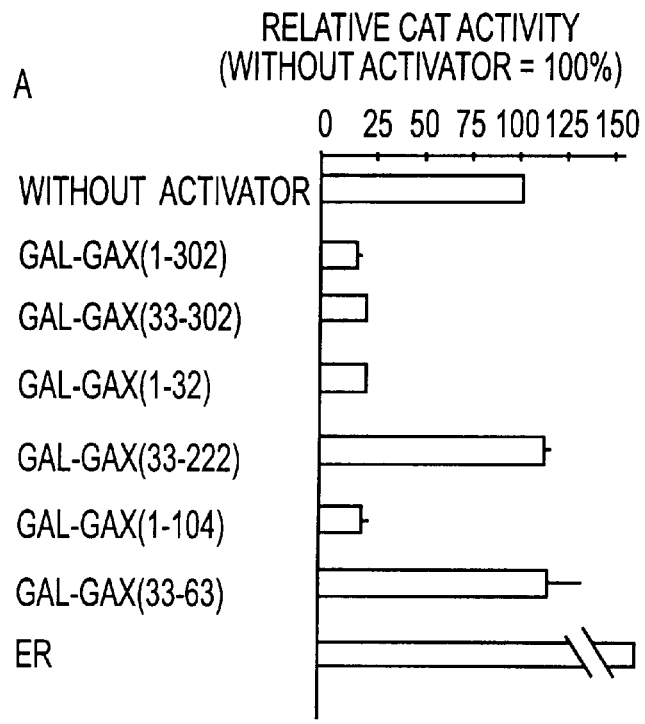
FIGS. 6A–6B: Determination of CAT enzymatic activity with different GAL-GAX chimeras.

Complete GAX, in the context of the GAL-GAX1-302 fusion, reduces CAT activity more than 8 times compared to the unactivated reporter. This repression is weakly affected when the 32 N-terminal amino acids of GAX are absent (GAL-GAX33-302), but it is increased completely when an additional deletion suppresses the C-terminal section of GAX (GAL-GAX33-222). In the context of GAL-GAXI-32, these 32 amino acids are sufficient to reduce CAT activity (FIG. 6A).

Figure 6B:
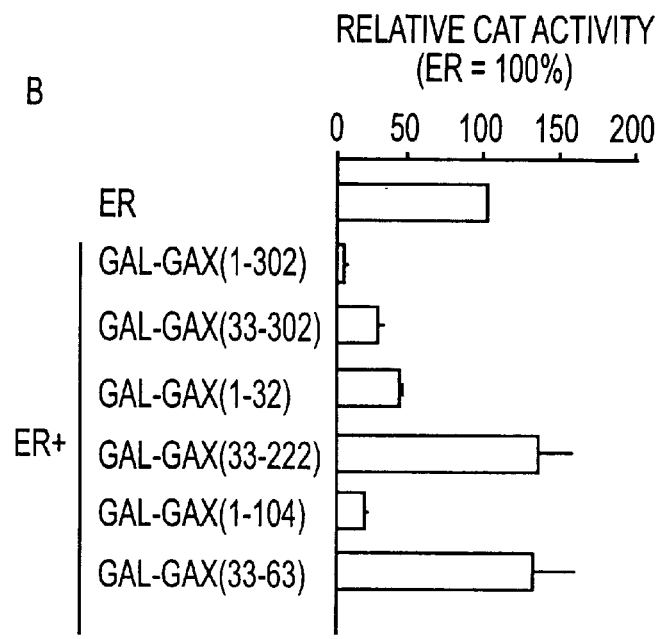

The coexpression of GAL-GAX1-302 and ER is the result of CAT activity more than 25 times less than that obtained with ER alone. As in A, This repression is due to the first 32 GAX amino acids (compare GAL-GAX1-302, GAL-GAX33-302 and GAL-GAX33-222). These 32 N-terminal amino acids (GAL-GAX1-32) reduce ER activity only 2-fold (compare GAL-GAX1-32, GAL-GAX1-104) and at a minimum require the presence of residues 33 to 222 for maximum activity (FIG. 6B).

The sequences that [lead to] decreased activity when they are absent are sought, leading us to conclude that they are necessary, but not sufficient, for interaction.

The results presented show that GAX represses the transcription of the reporter gene that is used. This repression is essentially due to an N-terminal peptide (1 to 32) whose optimal activity requires the presence of region 33 to 222 of GAX, and preferably, the presence of region 33–104 of Gax.

By using different GAX deletions fused to the DNA-binding domain of GAL4, we were able to identify in yeast (by the double hybrid system, Example 5) the GAX regions that are important for interaction with Ki. This is the N-terminal section up to residue 222. As we have demonstrated above, this region includes the GAX repressor domain.

Example 13
In Vitro Interaction Between GAX and PCNA 13.1. Cloning cDNA from the Human "Proliferating Cell Nuclear Antigen" (PCNA) and Production of a Recombinant Protein Cloning of cDNA from PCNA takes place via reverse transcription and PCR. The first step of reverse transcription (RT) is carried out with the "First Strand cDNA Synthesis Kit" from Pharmacia. Total RNA is extracted from human smooth muscle cells in a primary culture (Clonetics) according to the method described by P. Chomczynski and N. Sacchi (*Annal. Biochem.* 1987, 162: 156–159). Ten $\mu$g of this complete RNA is dissolved in 20 $\mu$l of water [and] heated for 10 minutes at 65° C., cooled on ice, then mixed with 11 $\mu$l of "Bulk First Strand Reaction Mix" from the RT kit (Cloned, FPLCpure®, Murine Reverse Transcriptase, RNase/DNase-Free BSA, dATP, dCTP, dGTP, and dTTP), 1 $\mu$l of DTT and 1 $\mu$l of pD(N)$_6$ primers. The RT reaction is incubated for 1 hour at 37° C. The reaction is stopped by heating for 5 minutes at 90° C., followed by cooling on ice.

The second step consists of amplification by PCR of the PCNA cDNA. The following primers are used for the PCR reaction:

```
1   5'-CGCGgaattcTGTTCGAGGCGCGCCTGGTCCAGG-3'  SEQ ID NO: 10
           F   E   A   R   L   V   Q   G   SEQ ID NO: 11
2   5'-GGTCgaattcTAAGATCCTTCTTCATCCTCGATC-3'  SEQ ID NO: 12
             *   S   G   E   E   D   E   I   K   SEQ ID NO: 13
```

The two primers introduce an EcoRI site (underlined lower case letters). The amino acids of PCNA contained in the primers are represented by their code (upper case letters) below the corresponding codons. * represents the PCNA stop codon.

Eight μl of the RT reaction, described above, are completed to obtain a total volume of 50 μl containing the following total quantities or concentrations: 50 picomoles of primer 1, 50 picomoles of primer 2, one unit of Taq DAN polymerase (Perkin Elmer), 5 μl of $MgCl_2$ (25 mM), 2 μl of a 200 mM mixture of the 4 deoxynucleotides (dATP, dTTP, dGTP and dCTP), and 5 μl of PCR buffer concentrated 10-fold (Perkin Elmer).

The PCR amplification takes place in Micoamp™ tubes (Perkin Elmer) using a PTC-100™ thermocycler (MJ Research, Inc.). This amplification consists of a denaturation step at 95° C. for 2 minutes, followed by 30 cycles that include a denaturation step lasting 15 seconds at 95° C., a hybridization step for 30 seconds at 55° C. and an extension step for 1 minute at 72° C. These thirty cycles are followed by an additional extension of 5 minutes, then the PCR reactions are stored at 10° C.

The practical implementation of PCNA cloning in the PCRII vector (Invitrogen) is carried out with the "Original TA Cloning® Kit" (Invitrogen). Three μl of PCR product, 1 μl of ligation buffer 10X, 2 μl of pCRII vector (25 ng/μl), 3 μl of water and 1 μl of T4 DNA ligase are incubated at 16° C. for 16 hours.

Two ml of this ligation reaction are used to transform competent TG1 bacteria as previously described. The bacteria are then cultured at 37° C. for 16 hours on a solid LB medium containing 1.5% Agar, 100 μg/ml of ampicillin in the presence of X-gal for the blue-white selection of recombinant clones (alpha complementation of β-galactosidase).

The recombinant clones (white colonies) are taken up in 10 μl of water and confirmed under the same conditions as the PCR after the RT reaction described above, except that triton X-100 at a final concentration of 0.01% v/v is added to the reaction.

Several positive clones are used for the DNA mini-preparations, including the ones in which the 5' section of the PCNA insert positioned downstream from the EcoRV site of pCRII are sequenced and retained for the next cloning step.

Cloning of PCNA in plasmid pET29 is carried out in the following manner: the PCNA EcoRV-Hind III fragment obtained from PCRII-PCNA is inserted at the level of the EcoRV-Hind III site of pET-29. This plasmid is then used for the production of the recombinant protein chimera S-PCNA. The steps used for the transformation, production and purification of S-PCNA are identical to the ones used for the production of the Ki antigen fused to the myc epitope.

13.2 Study of the In Vitro Interaction of GAX with PCNA

This study was conducted by following the same method used in Example 9 to study the interaction between the recombinant GST-GAX and SmycKi proteins.

Increasing amounts of recombinant GST and the GST-GAX chimera (50, 250, 500 and 750 ng) were separated on a 14% denaturing polyacrylamide gel containing (Novex). The proteins were transferred from the gel to a nitrocellulose membrane, which was then incubated in a solution containing the recombinant protein S-PCNA, followed by immunolabelling of PCNA using an anti-PCNA monoclonal antibody (Santa Cruz).

Figure 7:
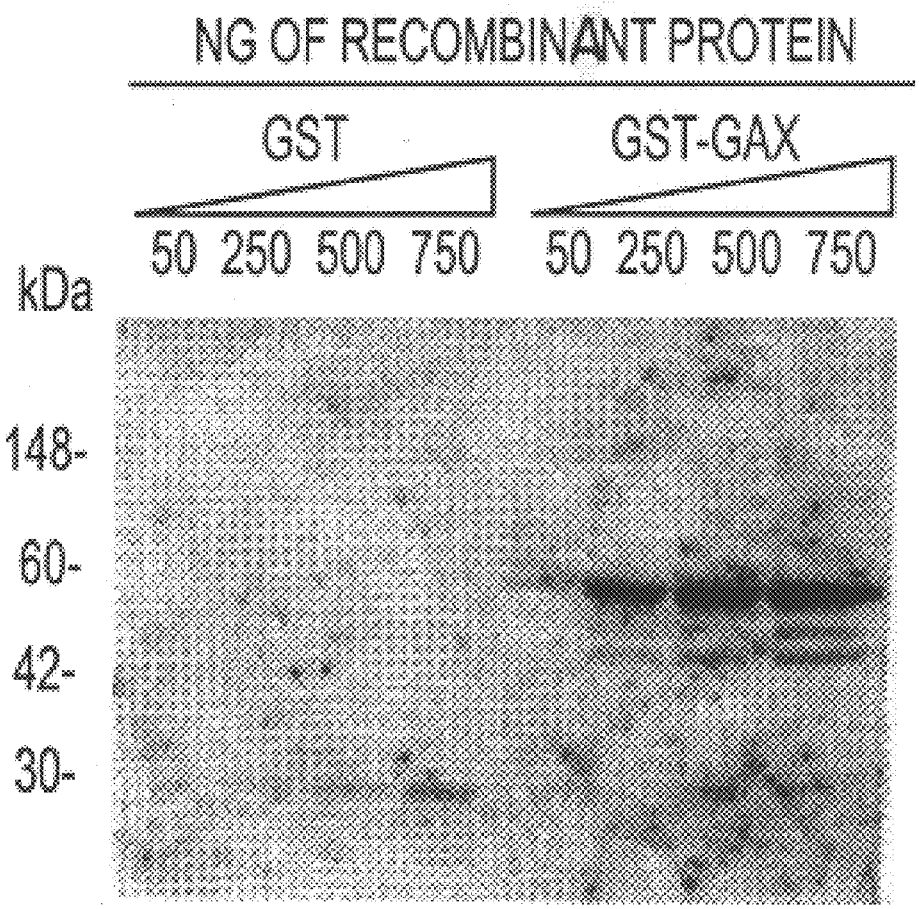
FIG. 7: Interaction between GST-GAX and PCNA.

FIG. 7 shows a weak interaction between GST and PCNA only with high doses of GST (500 and 750 ng). GST-GAX affinity for PCNA is clearly much higher than that with GST.

This specific interaction between GAX and PCNA suggests that the antiproliferative activity of GAX is mediated by PCNA sequestration. The fact that Ki can interact with both GAX and PCNA suggests the formation of bi- or tripartite complexes which might play an important role (activation or inhibition) in the progression of the cell cycle.

What is claimed is:

1. A polypeptide fragment of human GAX protein comprising a polypeptide fragment that represses transcription.

2. The polypeptide fragment according to claim 1, comprising residues 1 to 32 of human GAX protein as shown in SEQ ID NO. 16.

3. The polypeptide fragment according to claim 1, comprising residues 1 to 104 of human GAX protein as shown in SEQ ID NO. 16.

4. A composition comprising the polypeptide fragment according to claim 1.

5. A polypeptide fragment of human GAX protein comprising residues 1–32, 33–302 or 1–104 of human GAX protein as shown in SEQ ID NO. 16.

6. A polypeptide fragment comprising residues 1 to 32 or residues 104 to 223 of human GAX protein as shown in SEQ ID NO. 16.

7. A polypeptide comprising a fragment of a human GAX protein that represses transcription and at least one polypeptide fragment of a different origin.

8. The polypeptide according to claim 7, wherein the fragment of a different origin is a detectable marker or a targeting element.

9. The polypeptide according to claim 7, comprising residues 1–32 of human GAX protein as shown in SEQ ID NO. 16.

10. A method of screening for polypeptides that bind a GAX protein or a GAX protein domain, said method comprising incubating a sample with a polypeptide fragment of a GAX protein, and immunodetection of binding between a polypeptide in the sample and the polypeptide fragment of a GAX protein.

11. The method according to claim 10, wherein the polypeptide fragment of a GAX protein comprises residues 1 to 32 or residues 33 to 302 of a GAX protein.

* * * * *